United States Patent [19]
Gaynor et al.

[11] Patent Number: 5,350,835
[45] Date of Patent: Sep. 27, 1994

[54] CELLULAR NUCLEIC ACID BINDING PROTEIN AND USES THEREOF IN REGULATING GENE EXPRESSION AND IN THE TREATMENT OF AIDS

[75] Inventors: Richard B. Gaynor, Dallas; Foon K. Wu, Carrollton, both of Tex.

[73] Assignee: Board of Regents, University of Texas, Austin, Tex.

[21] Appl. No.: 788,266

[22] Filed: Nov. 5, 1991

[51] Int. Cl.$^5$ ............................................. A61K 37/10
[52] U.S. Cl. ................................... 530/358; 530/350; 435/974; 930/221
[58] Field of Search ................ 435/974; 530/350, 358; 930/221

[56] References Cited
PUBLICATIONS

Wu et al tat Regulates Bonding of the HIV . . . TRP-185 (reference AR) Genes & Development 5:2128-2140 1991.
Garcia et al. (1989), *The EMBO Journal*, 8(3):765-778, Human immunodeficiency virus type 1 LTR TATA and TAR region sequences required for transcriptional regulation.
Marciniak et al. (1990), *Cell*, 63:791-802, HIV-1 TAT Protein Trans-Activates Transcription In Vitro.
Berkhout et al. (1989), *Cell*, 59:273-282, Tat Trans-Activates the Human Immunodeficiency Virus Through a Nascent RNA Target.
Laspia et al. (1990), *Genes & Development*, 4:2397-2408, Synergy between HIV-1 Tat and adenovirus E1A is principally due to stablization of transcriptional elongation.
Marciniak et al. (1990), *Proc. Natl. Acad. Sci. USA*, 87:3624-3628, Identification and characterization of a HeLa nuclear protein that specifically binds to the trans-activation-response (TAR) element of human immunodeficiency virus.
Garcia et al. (1987), *The EMBO Journal*, 6(12);3761-3770, Interactions of cellular proteins involved in the transcriptional regulation of the human immunodeficiency virus.
Gaynor et al. (1989), *Proc. Natl. Acad. Sci. USA*, 86:4858-4862, Specific binding of a HeLa cell nuclear protein to RNA sequences in the human immuodeficiency virus transactivating region.
Harrich et al. (1990), *The EMBO Journal*, 9(13):4417-4423, TAR independent activation of the human immunodeficiency virus in phorbol ester stimulated T lymphocytes.
Roy et al. (1990), *Genes & Development*, 4:1365-1373, A bulge structure in HIV-1 TAR RNA is required for Tat binding and Tat medicated trans-activation.

(List continued on next page.)

Primary Examiner—Christine M. Nucker
Assistant Examiner—Jeffrey Stucker
Attorney, Agent, or Firm—Arnold, White & Durkee

[57] ABSTRACT

The invention relates to a cellular protein which is specific and has high affinity for nucleic acid sequences characteristic of an intact TAR RNA loop sequence of the HIV LTR TAR region. The invention also relates to a between 1,000–10,000-fold purified, about 185 kD protein preparation isolated from a mammalian cell nuclear extract preparation, most specifically a HeLa cell extract. The about 185 kD protein is shown to regulate HIV viral gene expression by binding a TAR RNA region of an HIV LTR template, in the presence of a cofactor fraction (including at least a~100 kD cofactor), and a tat protein. The TRP-185, having a molecular weight of about 185 kD protein may also provide a research tool in the study of viral and cellular gene expression. A route for the development of immunodiagnostics for AIDS and related disorders may also be provided given the specific and high affinity of TRP-185 for HIV RNA. The 185 kD protein and related encoding amino acid and DNA sequences may also be used in therapeutic agents for AIDS and related disorders and, for the generation of specific antibodies for use in the diagnosis and study of the epidemiology of AIDS.

16 Claims, 15 Drawing Sheets

PUBLICATIONS

Pearson et al. (1990), *Proc. Natl. Acad. Sci. USA*, 87:5079–5083, A transdominant tat mutant that inhibits tat-induced gene expression from the human immunodeficiency virus long terminal repeat.

Wu et al. (1988), *The EMBO Journal*, 7(7):2117–2129, Purification of the human immunodeficiency virus type 1 enhancer and TAR binding proteins EBP-1 and UBP-1.

Dignam et al. (1983), *Nucleic Acids Research*, 11(5):1475–1488, Accurate transcription initiation by RNA polymerase II in a soluble extract from isolated mammalian nuclei.

Field et al. (1988), *Molecular and Cellular Biology*, 8(5):2159–2165, Purification of a RAS-Responsive Adenylyl Cyclase Complex from Saccharomyces cerevisiae by Use of an Epitope Addition Method.

Gatignol et al. (1989), *Proc. Natl. Acad. Sci. USA*, 86:7828–7832, Identification of cellular proteins that bind to the human immunodeficiency virus type 1 trans-activation-responsive TAR element RNA.

Goody et al. (1991), *FEBS Letters* (pp. 1–5), Factors contributing to the inhibition of HIV reverse transcriptase by the chain-terminating nucleotides in vitro and in vivo.

Calnan et al. (1991), *Genes & Development*, 5:201–210, Analysis of arginine-rich peptides from the HIV Tat protein reveals unusual features of RNA-protein recognition.

Gaynor (1991), Role of the TAR Element in Regulating HIV Gene Expression, In: *Advances in Molecular Biology and Targeted Treatment of AIDS*, pp. 79–90.

Gaynor, R. (1991), Cellular Factors Involved in Regulating HIV Gene Expression, In: *Genetic Structure and Regulation of HIV*, Haseltine and Wong-Staal, editors: pp. 107–134.

Waterman et al. (1991), Nuclear Proteins Implicated in HIV-1 Transcriptional Control, In: *Genetic Structure and Regulation of HIV*, Haseltine and Wong-Staal, editors: pp. 391–403.

Wu et al. (1991), Genes and Development, 5(11)1935–2152, tat Regulated Binding of the Human Immunodeficiency Virus Trans-Activating Region RNA Loop-Binding Protein TRP-185.

Sheline et al. (1991), Genes and Development, 5(12b):2508–2520, Two distinct nuclear transcription factors recognize loop and bulge residues of the HIV-1 TAR RNA hairpin.

Gaynor, R. (1992), AIDS, 6(4):347–363, Cellular transcription factors involved in the regulation of HIV-1 gene expression.

International Search Report, No. 92/09546.

Dialog Search Report (1991).

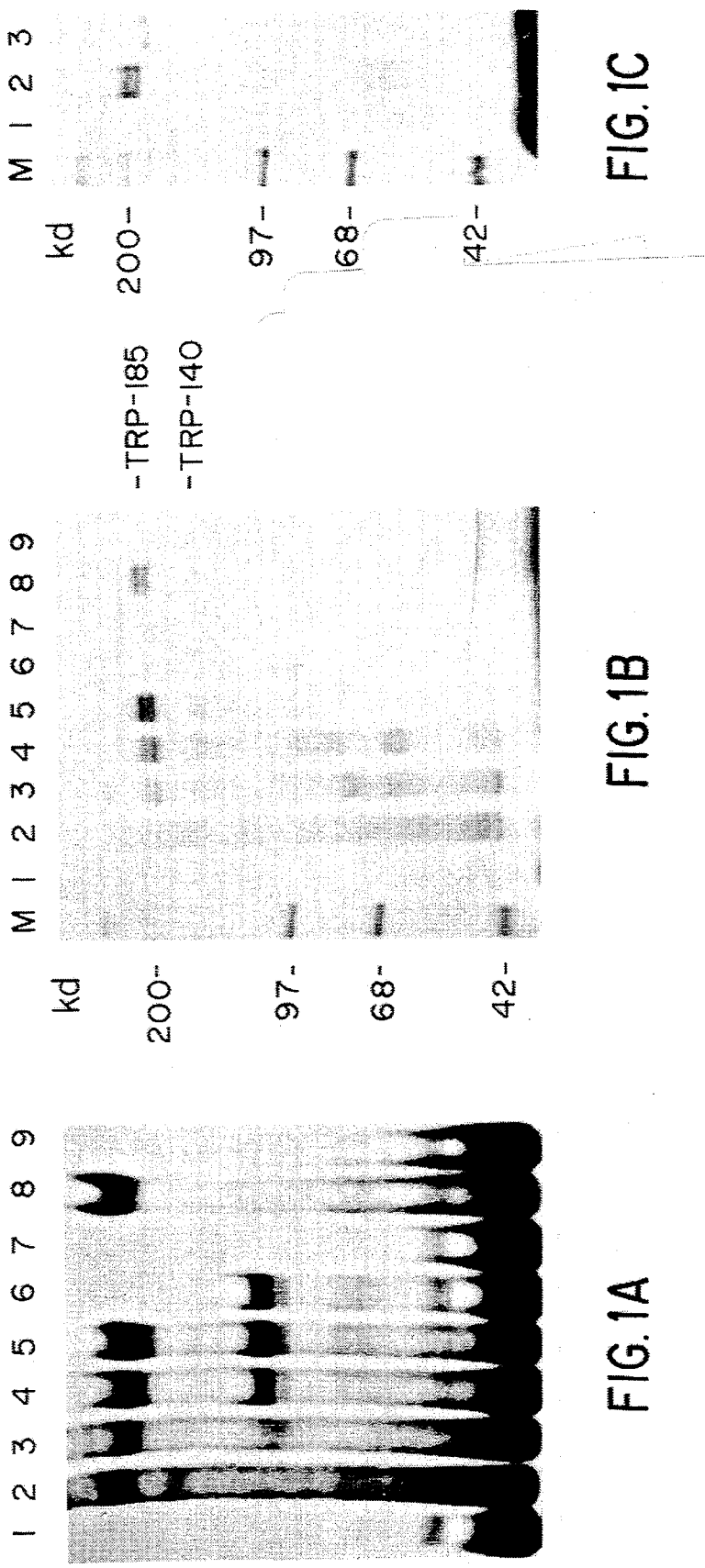

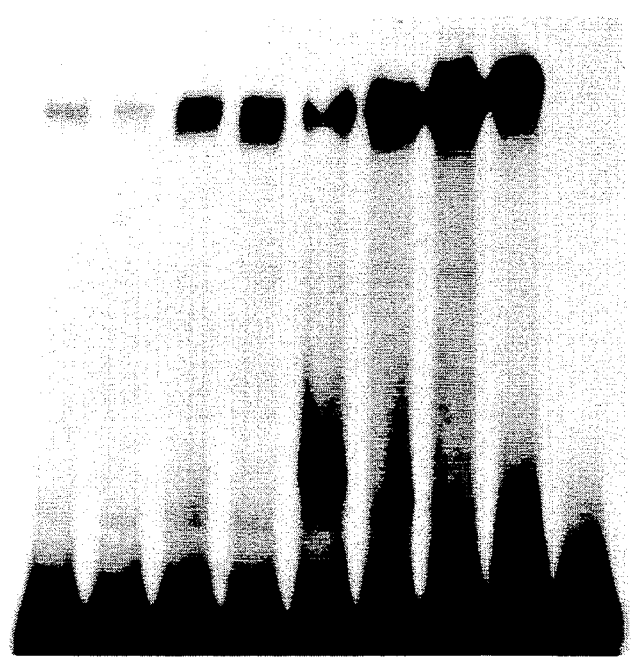
FIG. 9C
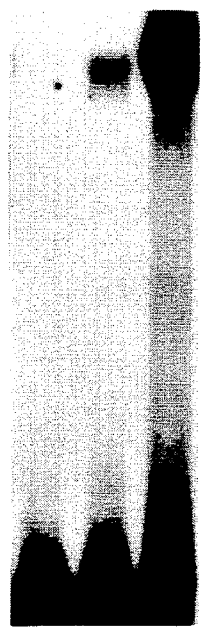
FIG. 9D
FIG. 9E
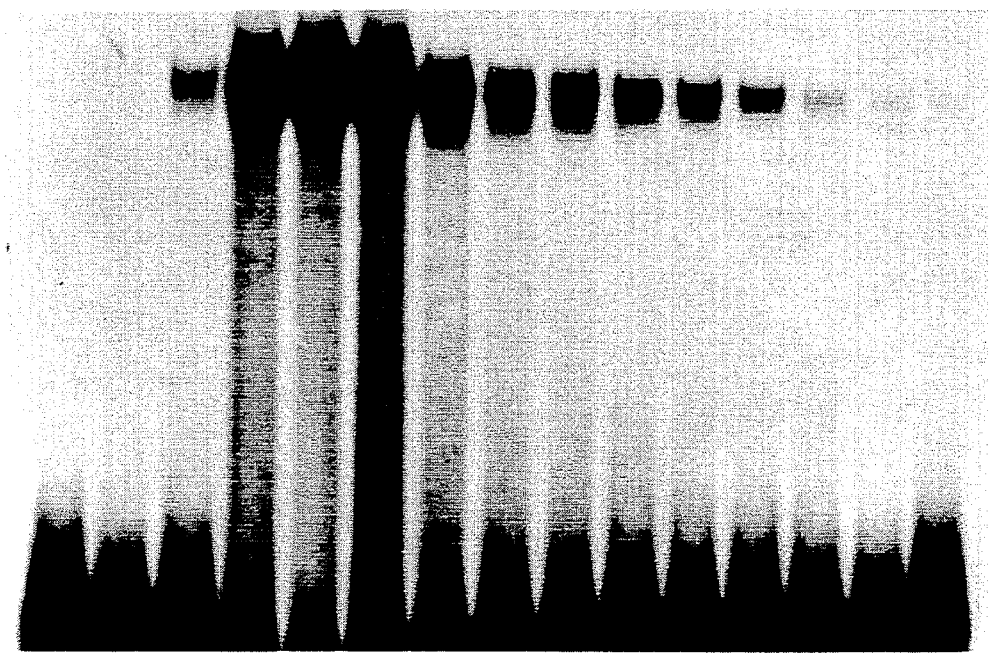

CELLULAR NUCLEIC ACID BINDING PROTEIN AND USES THEREOF IN REGULATING GENE EXPRESSION AND IN THE TREATMENT OF AIDS

The government may own rights in the present invention as research relevant to the development thereof was supported by grants from the United States government, NIH Grant AI25288.

BACKGROUND OF THE INVENTION

1. Field of the Invention

The invention relates to the field of cellular proteins, most particularly cellular proteins capable of binding nucleic acids and regulating gene expression. In addition, the invention also relates to the field of reagents useful in the characterization of viral and cellular gene expression, as the disclosed cellular protein is demonstrated to bind to a particular viral RNA region important in viral gene expression. The invention also relates to the field of therapeutic methods and reagents for the treatment of viral diseases, such as AIDS. Methods and reagents (including monoclonal antibodies) for screening/detecting viral infection in a biological sample are also within the field of the present invention.

2. Background of the Related Art

Gene expression of the human immunodeficiency virus (HIV) is regulated by a variety of mechanisms. The long terminal repeat (LTR) is the site of multiple regulatory regions involved in both general and tissue specific gene expression.[1-16] Two regions, including the NFAT[17,18] and NF-kappa B motifs[4,19,20] are involved in the regulation of the HIV LTR in activated T-lymphocytes. Other elements such as SPI[2,11] and TA-TA[3,7,10] are involved in regulating gene expression in a variety of both lymphoid and nonlymphoid cell lines.

HIV contains an additional regulatory element known as the transactivating region, TAR, which extends from $-17$ to $+80$ in the HIV LTR.[1,3,5-7]

The TAR element is required for activation of gene expression by the viral transactivator protein, tat.[9,12,20-25] The structural integrity of TAR RNA is a key element for tat activation.[5,12,6,9] TAR RNA is capable of forming a stable stem-loop structure and disruption of stem base pairing results in a marked decrease in tat activation. However, compensatory mutations which restore stem base pairing result in nearly wild-type levels of tat activation.[5,6,15] The loop and bulge regions in TAR are also required for high level activation by tat.[5,13,27] Substitution of single base pairs in the loop decreases tat activation while substitution of multiple base pairs in this region result in even further decreases in tat activation.[9,10,15] Deletion of the bulge region, or substitution for a single "U" residue at $+23$ in the bulge, also severely decreases tat activation.[15,16,27] Thus, three major determinants including the stem, loop, and bulge are each required for wild-type activation of the TAR element and ultimate gene expression of HIV.

Recently, a number of studies indicate that the tat protein, via its basic domain, is capable of binding to the bulge region in TAR RNA.[16,27-29] A variety of nuclear proteins are also capable of binding to TAR RNA.[30-32] However, the role or importance of these "binding" proteins, particularly for the regulation of gene expression, has not been fully characterized.

A previous study used UV-crosslinking assays to identify a 68 kDa cellular protein that binds specifically to the TAR loop region.[26] Using similar techniques, the present inventors also detected a 68 kDa cellular protein which binds to TAR RNA. The detection of this protein was dependent on the use of heparin and ribonuclease following the binding reactions. However, when nonspecific RNA or poly (I)-poly (C) was used in gel retardation assays without ribonuclease, this species was no longer detected (unpublished results). Another RNA binding protein, TRP-140, which binds with high affinity to a variety of double-stranded RNAs, may also potentially have functional significance in regulating HIV gene expression.

Several viruses, such as those of the HIV and the HTLV (human leukemia/lymphoma virus) type, have within their gene structure a downstream regulatory region that is required for transactivation (a protein that acts in conjunction with a viral protein as a transactivating factor—the pX region[49]) to which a cellular protein binds. A more complete understanding of the mechanisms which govern viral gene expression, most particularly the role of particular binding proteins for the TAR region in expression, would provide a route whereby methods for selectively "turning on" and "turning off" of genes employing important cellular proteins could be accomplished. Most importantly, in the case of viral infections such as AIDS, such information could be employed to develop a therapeutic agent which selectively "turned off" the expression of HIV and HTLV in an animal.

HIV is recognized as the causative agent of Acquired Immunodeficiency Syndrome (AIDS). Therapeutic agents which have been used in the treatment of AIDS include AZT (azidothymidine) and DDI (dideoxyinosine).[33] Both of these agents are nucleotide analogs that target the viral enzyme, reverse transcriptase. While these agents have been used with varying degrees of success, they are also unfortunately associated with a variety of severe side effects. Some of these side effects include peripheral neuropathy (DDI), pancreatitis, granulocytopenia, anemia, severe headache, nausea, insomnia, neurotoxicity, seizure, as well as being associated with a potential carcinogenicity and teratogenicity.[33]

Other molecular targets for anti-viral therapy under investigation include an HIV-gene encoded protease. The protease is encoded on the polygene of HIV-1. The polygene encodes three proteins—a reverse transcriptase, a self-cleaving protease that is required for processing the reverse transcriptase, and a nuclease that is essential for integration of viral DNA into the genome of the host cell. Inhibitors of the HIV protease have been developed with the aid of a crystal structure of the protein.

Other potential molecular targets described include the glycosolated envelope protein of HIV and the receptor protein (CD4) on the surface of lymphocytes to which the virus binds. A soluble form of CD4 can bind to the viral envelope protein and prevent the virus from entering cells. Alternatively, a conjugate of CD4 and a toxin might be used to attack HIV-infected cells, since such cells express the envelope protein on their surfaces. Another drug, dextran sulfate, has also been used in the treatment of AIDS for its ability to block the binding of HIV to target cells.

However, none of the aforedescribed molecular targets for anti-viral therapy relates to use of a molecular agent of cellular origin which specifically affects viral gene expression. An enhanced understanding of the particular role of cellular proteins in the molecular events of both cellular and vital (HIV) gene expression would provide a new avenue for the development of effective anti-viral agents. Such information would further provide for the development of a new genus of drugs based on the regulation of host proteins for the treatment of diseases such as AIDS and AIDS-related diseases.

The present inventors have characterized a particular cellular protein designated "TRP-185", which possesses botch high affinity and marked specificity of binding to a viral TAR RNA region in a manner that correlates with in vivo genetic data in that the TRP-185 cellular protein only binds to templates that are activated by the transactivating protein.

Thus, a solution to providing for the specific inhibition activation of viruses, such as HIV and HTLV, which have a downstream binding region for important cellular proteins important in gene activation is disclosed.

It is an object of the invention to provide a tool which is useful in the characterization of viral and cellular gene expression. It is still another object of the invention to provide a reagent which is useful in the study of viral gene regulation.

It is still a further object of this invention to provide a better, more reliable and convenient procedure for testing human serum and plasma for presence of the AIDS virus.

It is another object of the invention to provide a method for monitoring the progression and treating HIV-disease in a patient. How these and other objects of this invention are achieved will become apparent in light of the accompanying disclosure. In at least one embodiment of the practices of this invention, at least one of the foregoing objects will be achieved.

SUMMARY OF THE INVENTION

The present invention addresses one or more of the foregoing or other problems associated with the characterization and control of gene expression, most particularly viral HIV gene expression. The present invention also addresses the need for alternative AIDS and AIDS-related disease therapeutic agents which target particular molecular events of HIV gene expression by controlling for the activity of a cellular protein, designated herein as a "TRP-185" protein.

The invention provides for the preparation and use of specific cellular protein antigens, particularly those antigens associated with the activation of HIV expression, and which would be useful in the development of diagnostic methods for HIV infection. The invention involves the identification of the above designated cellular protein, which has been found to be an important regulatory protein of viral gene expression. The invention also identifies and provides for the isolation of cellular proteins and particular cellular "cofactors" important in facilitating viral gene binding and HIV gene expression.

The identification of these particular cellular proteins will provide for characterization of their corresponding nucleic acid sequences. Knowledge of the sequences which encode the TRP-185 protein will be useful in the preparation of expression vectors for transforming whole cells to produce recombinant cellular protein antigenic polypeptides. These recombinant proteins may be employed as a reagent in the molecular characterization of gene expression. It is further proposed that the cellular proteins demonstrated to be important in HIV gene expression will be useful in the preparation of immunodiagnostic agents and therapeutic agents (i.e. inhibitors) for the treatment of HIV-related diseases (i.e. AIDS, ARC, ALT (adult T-cell leukemia/lymphoma)).

The present invention, more specifically, provides a particularly defined nucleic acid binding element comprising a cellular protein capable of binding with specificity and high affinity to a TAR region of nucleic acid. Even more particularly, the inventors demonstrate that the particular nucleic acid binding element will bind to an TAR region of the HIV RNA in the presence of a cofactor fraction.

For purposes of describing the present invention, the nucleic acid binding element has been designated "TRP-185". This particular designation was derived from characterization of the TRP-185 cellular protein as having a molecular weight of between about 175–190 kD. Even more specifically, the molecular weight of the TRP-185 is about 185 kD (silver stained gel—see FIG. 10). The TRP-185 binding protein identified in these analysis has been determined to be in a monomer form. Binding of the TRP-185 protein provides for the activation of the trans-activating region of the viral RNA, and gene expression of the viral tat trans-activator protein occurs.

The nucleic acid binding element TRP-185 may be useful alone as a tool for elucidating mechanisms of HIV and cellular gene expression. It has been demonstrated that TRP-185 requires the presence of elements in a "cofactor" fraction to bind the TAR region of HIV RNA. The "cofactor" fraction is defined, for purposes of describing the present invention, as a composition including at least one cofactor having a molecular weight of between about 85–100 kD. However, the elements present in the "cofactor" fraction do not themselves bind to the TAR RNA binding site.

In the presence of the "cofactor" fraction, the TRP-185 binds with specificity and high affinity to a particular region of the HIV RNA, designated the TAR region of the long terminal repeat (LTR) of mRNA. Even more particularly defined, the TRP-185 cellular protein binds to a TAR (transactivating) region of the HIV mRNA with an affinity of about $3 \times 10^{-10}$M.

Binding of the TRP-185 to the TAR region of HIV RNA is shown to increase transcription of wild-type HIV LTR, thus increasing the replication of the virus by about 4-fold. As used in the description of the present invention, the term "TAR region" is defined as a transactivating region of a nucleic acid, most specifically a TAR region of the HIV mRNA LTR. The TAR region bound by the nucleic acid binding element (i.e. TRP-185) comprises an at least 12 base-pair segment of the TAR mRNA region. Defined in terms of the particular base pairs of the TAR mRNA, the TRP-185 cellular protein may be described as binding a base-pair segment between bases 23–34 of the TAR mRNA. The sequence of the TAR region of HIV RNA is provided in FIG. 3.

The present invention also includes a highly efficient method for isolating and preparing the cellular protein found to bind a TAR mRNA region of HIV. In one particularly preferred embodiment, the nucleic acid binding element of the present invention may be prepared by a process comprising the steps of obtaining a volume of mammalian cells, preparing a nuclear extract from the mammalian cells and fractionating the nuclear extract and selecting fractions having TAR binding activity and isolating an element having a molecular weight of between 175–190 kD from the selected fractions to provide a nucleic acid binding element.

Even more particularly, fractionating the nuclear extract to obtain the TRP-185 nucleic acid binding element includes the steps of chromatographing the nuclear extract on heparin agarose, eluting the chromatographed nuclear extract with potassium chloride to obtain TAR active binding fractions, selecting TAR active binding fractions and obtaining a dialysate thereof, chromatographing the dialysate on a HTP Bio gel, precipitating TAR active binding fractions from the HTP Bio gel with ammonium sulfate, applying the TAR active binding fractions to a Superdex 200 FPLC column, collecting TAR active binding fractions and applying a dialysate of selected fractions therefrom to a Bio Rex column, collecting HIV active binding fractions and applying a dialysate thereof to a Dextran Blue Sepharose column, collecting TAR active binding fractions and applying a dialysate thereof to a Mono Q FPLC column, collecting TAR active binding fractions and applying a dialysate of selected washed fractions to a continuous sucrose gradient, and isolating a nucleic acid binding element having a molecular weight of between 175 kD–190 kD as determined by a continuous sucrose gradient, said element having TAR region binding activity.

The term "TAR active binding" as used in the description of the present invention relates to the ability or the demonstration of the ability of a particular sample or elements within a sample or column fraction to bind the TAR region of a nucleic acid, such as DNA or RNA, which is even more specifically described as a binding activity for the TAR region of the HIV mRNA LTR.

Any of a variety of mammalian cells may be used to prepare the nuclear cell extract. By way of example, such particularly useful mammalian cell lines include VERO (ATCC CCL 81) and HeLa cells (ATCC CCL 2.1, ATCC CCL 2.2), the W138, COS, Jurkat, CEM, 293 (human embryonic kidney cell line ATCC CRL 1573) and MDCK cell lines. Most preferably, the mammalian cell line employed to prepare a mammalian cell nuclear extract for purposes of isolating the herein described binding protein TRP-185 is the HeLa cell line.

Employing the above described process, a TRP-185 binding protein preparation having a purity of about 3,000 fold, and a high yield of about 10–15% is provided from a HeLa cell nuclear extract. The high yield provided by the herein described preparation presents a significant advantage of the present invention over the art, as using other preparation schemes (which include an S-300 column), in which up to 95% of the protein will be lost (inventors unpublished observations).

In still another aspect of the invention, a method for preparing a cellular protein having binding affinity for all HIV TAR region is provided. This method comprises the steps of preparing a nuclear extract having HIV TAR RNA binding activity from mammalian cells, fractionating the nuclear extract to select for HIV TAR binding activity, and isolating an HIV TAR binding element to provide the cellular protein, wherein said protein has a molecular weight of about 185 kD.

In the most particularly preferred embodiment of the described processes and methods of the present invention, fractionating the nuclear extract includes chromatographing the nuclear extract on heparin agarose, eluting the chromatographed nuclear extract by potassium chloride to obtain TAR active binding fractions, selecting and dialyzing TAR active binding fractions, chromatographing the active fractions on an HTP Bio gel, precipitating with ammonium sulfate and selecting TAR active binding fractions, applying the TAR active binding fractions on a Superdex 200 FPLC column, collecting TAR active binding fractions and applying a dialyzate of the active fractions to a Bio Rex column, collecting TAR active binding fractions and applying a dialyzate of the active fractions to a Dextran-Blue Sepharose column, collecting TAR active binding fractions and applying a dialyzate thereof to a Mono Q FPLC column, collecting TAR active binding fractions and applying a dialyzate of selected washed fractions to a continuous sucrose gradient, and isolating a nucleic acid binding element having a molecular weight of between 175–190 kD as determined by a continuous sucrose gradient having TAR region binding activity.

The method most preferably includes the preparation of a nuclear extract according to the steps of lysing a cell pellet of HeLa mammalian cells with a Dounce homogenizer, isolating nuclei from the cells, lysing the nuclei, centrifuging the lysate to obtain a supernatant, and dialyzing the supernatant to obtain a nuclear extract having a binding activity for a TAR region of nucleic acid.

The present invention in still another aspect defines an immunoassay for the detection of an antibody specific for a nucleic acid binding element TRP-185 in a biological sample. In one particular embodiment of the immunoassay, the immunoassay comprises; preparing a cellular binding protein specific for TAR RNA and which regulates HIV gene expression to provide a TRP-185 antigen, incubating the TRP-185 antigen with the biological sample for a sufficient time to permit binding between antigen and antibody present in said biological sample, and determining the presence of bound antibody by contacting the incubate of the antigen and antibody with a detectably labeled antibody specific for the anti-TRP-185 antibody, wherein the presence of anti-TRP-185 antibody in the biological sample is detectable as the measure of the detectably labeled antibody from the biological sample.

By way of example, the antibody may be labeled with any of a variety of detectable molecular labeling tags. Such include, an enzyme linked antibody, a fluorescent tagged antibody, or a radio-labelled antibody. In one particular embodiment of the described immunoassay, the TRP-185 is prepared from mammalian cell nuclei or a recombinant host expressing said TRP-185 antigen. In the described immunoassay, the presence of anti-TRP-185 antibody is diagnostic of an HIV viral infection in the animal. Use of a cofactor-exposed TRP-185 antigen and a cofactor unexposed TRP-185 antigen in the immunoassay may also provide a method for monitoring the progression of an HIV infection in an animal, as it is postulated that the infected state of the animal will be reflected in the type of reactive antibody in the animal to each of these different TRP-185 preparations as antigen.

In still another aspect of the present invention, a nucleic acid sequence or fragment thereof encoding a cellular protein TRP-185 which binds an HIV TAR RNA is provided. The nucleic acid segment or fragment thereof is isolatable from most preferably human chromosomal DNA. The nucleic acid segment or fragment thereof is even more specifically defined as encoding an antigenic protein capable of producing an in vivo immunogenic response to the TRP-185 cellular protein.

The nucleic acid segment or fragment thereof may also be defined as a cDNA sequence complementary to a TRP-185 mRNA.

The present invention also includes a recombinant DNA vector which includes a DNA sequence encoding a nucleic acid binding element capable of binding with high affinity to a TAR RNA region in the presence of at least one cofactor. The nucleic acid binding element is of cellular origin and has a molecular weight of between about 175-190 kD. The recombinant DNA vector may also be described as including a DNA sequence which is a cDNA sequence complementary to a TRP-185 mRNA or a fragment thereof. The recombinant DNA vector of the present invention will also be capable of replication in a host.

A recombinant host bearing a recombinant DNA vector may also be prepared. The DNA sequence of the recombinant DNA vector may be defined further as a cDNA sequence which is complementary to a TRP-185 mRNA. The recombinant host should also be capable of expressing the DNA segment to produce a TRP-185 cellular protein.

By way of example, the recombinant host of the present invention may be *Saccharomyces cerevisiae, Escherichia coli,* Bacculovirus or a Vaccinia Virus host.

Recombinant methods may also be utilized in obtaining the cellular protein having the binding affinity for nucleic acid sequences characteristic of the TAR RNA region of the HIV long terminal repeat. One particular embodiment for preparing a recombinant TRP-185 cellular protein comprises preparing a recombinant host bearing a recombinant DNA segment encoding a cellular TRP-185 protein capable of binding a TAR RNA; said recombinant host being capable of expressing the protein, culturing the recombinant host to produce TRP-185, and separating the TRP-185 from the recombinant host.

Still another aspect of the invention includes an antibody specific for a TRP-185 cellular protein having binding affinity for a TAR RNA region. The antibody may be either a monoclonal antibody (such as that produced by a hybridoma cell line) or a polyclonal antibody. Where the antibody is a monoclonal antibody, it may be defined further as having an IgG or IgM isotype.

The antibody of the present invention may be prepared by employing the TRP-185 cellular protein described herein together with a standard immunization protocols known to those in the art (see Example 3).

In still another embodiment of the invention, a hybridoma cell line which produces a monoclonal antibody which specifically binds a TRP-185 cellular protein is provided. Most particularly, the hybridoma cell line is a murine hybridoma cell line produced by immunizing a mouse with a cellular protein TRP-185 which binds an HIV TAR mRNA, isolating anti-TRP-185 antibody producing cells from the immunized mouse, and fusing the antibody producing cells with a neo-plastic murine cell line to obtain a murine hybridoma cell line.

Another aspect of the present invention provides a therapeutic agent for the treatment of HIV or HTLV infection in an animal. The therapeutic agent comprises an admixture of an inhibitor of a TRP-185 cellular protein in a pharmaceutically acceptable excipient. Most preferably, the therapeutic agent will be formulated so as to be suitable for administration as a parental formulation or as a capsule (for oral administration).

In still another aspect of the present invention, an RNA binding complex is provided. The RNA binding complex may be particularly useful in characterizing the molecular events of gene expression. In one particular embodiment, the RNA binding complex comprises a TRP-185 cellular protein capable of binding a TAR RNA region of HIV, at least one cofactor capable of facilitating the binding of the TRP-185 to a TAR RNA, and a volume of TAR RNA sufficient to bind the TRP-185. Most preferably, the cofactor is an about 100 kD protein isolatable from a mammalian cell extract. Most preferably, the cofactor and the TRP-185 cellular protein are isolated from a HeLa cell nuclear cell extract as previously described herein. It is anticipated that the described RNA binding complex may be used as a laboratory and research reagent, most particularly in the characterization of viral and cellular gene expression.

In still another embodiment, a diagnostic test pack for the detection of anti-TRP-185 antibody in a biological sample is provided. In one preferred embodiment, the diagnostic test pack comprises in packaged combination a carrier means adapted to receive at least three container means in close confinement therewith, a first container means including a TRP-185 cellular protein capable of binding a TAR RNA and having molecular weight of about 185 kD, a second container means including a quantity of an unlabeled antibody having specific binding affinity for the TRP-185 cellular protein, a third container means including a quantity of a detectably labeled antibody specific for binding with the anti-TRP-185 antibody, and at least one microtiter plate.

More specifically, the detectably labeled antibody of the described test-pack is an enzyme-linked antibody, a fluorescent tagged antibody or a radio-labeled antibody. By way of example, radiolabels such as $^{125}$I, $^3$H and other may be used to label the antibody.

The pack and still another embodiment may include a fourth container means having a quantity of a substrate for the enzyme sufficient to produce a visually detectable product, where the antibody of choice is an enzyme-linked antibody. Even more preferably, the antibodies of the diagnostic text pack are monoclonal antibodies specific for the TRP-185 cellular protein. Alternatively, both the unlabeled antibody and the detectably labeled antibody are polyclonal antibodies specific for the TRP-185 cellular protein.

The particular TRP-185 cellular protein of the present invention is expected to be important in the regulation of cellular genes as well as HIV and HTLV genes. Highly purified fractions of the TRP-185 cellular protein have been shown by the inventors to bind strongly to elements of cellular promoters downstream of important "initiation elements" (such as in the adenovirus). This activity demonstrates that the herein isolated TRP-185 cellular protein may have the ability to also regulate other gene promoters.

In particular embodiments of the described therapeutic agents, "inhibitors" of TRP-185 may in addition to the aforedescribed specific antibodies for TRP-185 include antisense DNA, an RNA fragment that preferentially binds the TRP-185 protein, a competitive binding protein for the TAR-RNA binding site, or a protein or a peptide which acts to modify a TRP-185 protein, such as to dephosphorylate the TRP-185 protein to thereby potentially prevent the binding of the TRP-185 to its specific TAR RNA binding site.

In that the present inventors have disclosed the ability of a cellular protein to bind to both upstream and downstream of important promotor elements to a highly conserved region of, for example, the HIV gene, the inventors postulate the particular TRP-185 cellular protein may also bind other "conserved" nucleic acid regions which become activated upon association with a cellular protein, to affect gene expression. These results indicate that TRP-185 binds to conserved regions of DNA known as "initiator sequences".[57] These elements are critical for gene expression of both viral and cellular genes. Thus, TRP-185 may regulate the expression of various cellular genes.

BRIEF DESCRIPTION OF THE DRAWINGS

FIGS. 1a-c Assay of TRP-185 and TRP-140 fractionation.

Fractions from chromatography that were active for binding to TAR RNA in gel retardation (FIG. 1A) or UV crosslinking assays (FIG. 1B) are shown. Lanes 1=probe alone; Lane 2=heparin agarose; Lane 3=Sephacryl S-300; Lane 4=mono S FPLC; Lane 5=hydroxylapatite; Lane 6=sucrose gradient TRP 140 pool; Lane 7=Sucrose gradient TRP 185 Pool; Lane 8=Sucrose gradient TRP 185 pool and cofactor (CF) fraction; and Lane 9=cofactor (CF) fraction alone. FIG. 1C: Lane 2 and Lane 3 show UV crosslinking of TRP-185 from the sucrose gradient TRP 185 fraction in the absence (lane 2), or presence (lane 3) of RNase.

FIG. 2 A=TRP-185 binding was assayed by gel retardation with fractions 5–19 obtained by analytical sucrose gradient centrifugation. FIG. 2B=These same fractions were also assayed in the presence of cofactors fractions. The positions of the migration of molecule mass markers in the sucrose gradient are shown.

The stem-loop structure of the HIV LTR extending from +1 to +62 is shown for a series of constructs which extend to +80 (Hind III) in the LTR. The (+1/+80) TAR DNA fragments were ligated to a linker encoding the T7 RNA polymerase promoter, the linker-TAR fragments were cloned into pUC19, and RNA transcription from these constructs was performed in vitro with T7 polymerase. The shaded areas indicate the nucleotides substituted and/or deleted in each construct. The constructs include (1) wild-type, (2) (+31/+34), (3) (TAR-sense), (4) +19/+22, (5) (+19/+22)/(+40/+43), (6)(+23), (7)Δ(+23/+25), (8) +30, (9) +32, and +34.

Figures 4A, 4B:
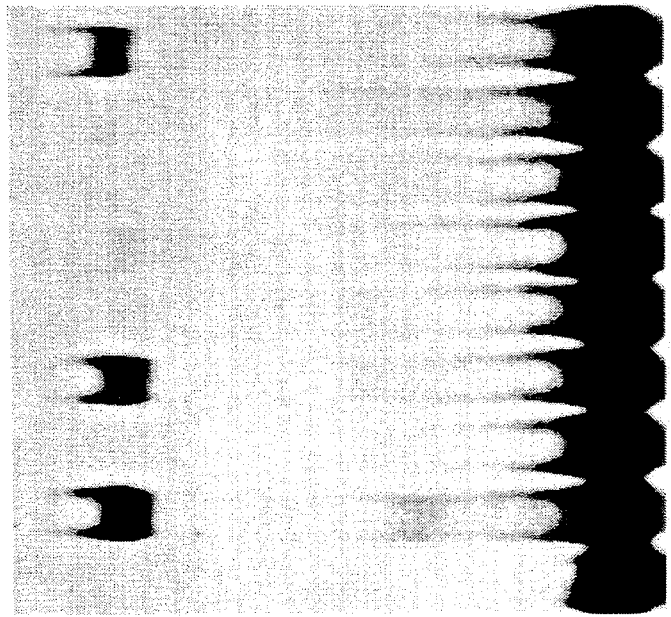
Figure 4C:
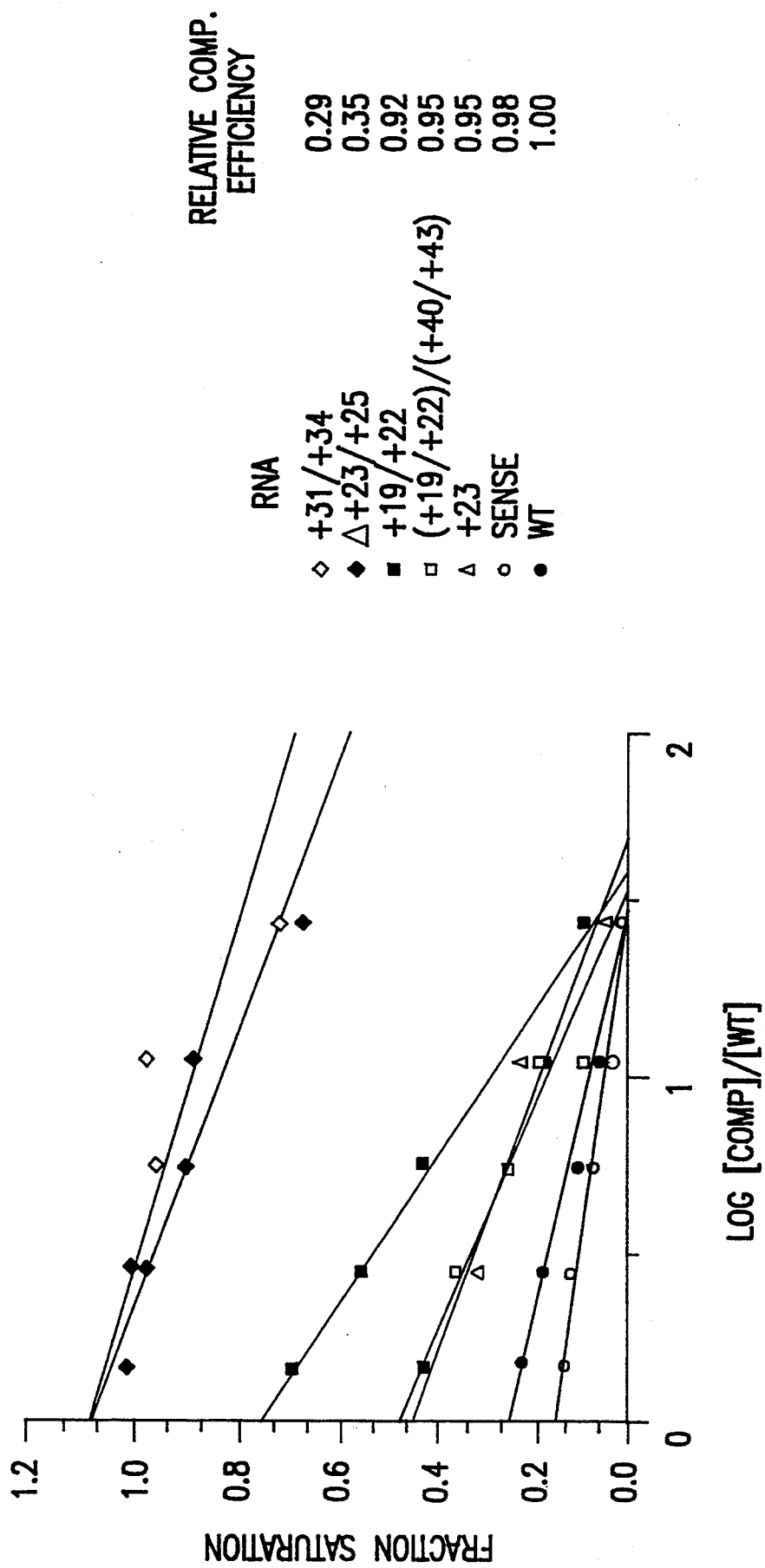

FIGS. 4a-c Competition analysis of TRP-185 and TRP-140 with mutant TAR RNA

Gel retardation analysis was performed with internally labeled wild-type TAR RNA and either hydroxylapatite (FIG. 4A) or analytical sucrose gradient (FIG. 4B) purified TRP-185 with added cofactors. Lanes include probe alone (lane 1), extract (lane 2), or competition with a 30-fold excess of unlabeled RNA for wild-type (Lane 3); +31/+34 (Lane 4); TAR-sense (Lane 5); 19/+22, (Lane 6); (19/+22) / (+40/+43) (Lane 7); +23 (Lane 8); and Δ(+23/+25) (Lane 9). Binding reactions were performed by mixing various amounts of competitor RNA (0–50 ng) with 1.5 ng of wild-type RNA probe and the added extract. FIG. 4C=Experimental data were plotted, and competition curves and relative competition efficiencies were determined.

Figure 5B:
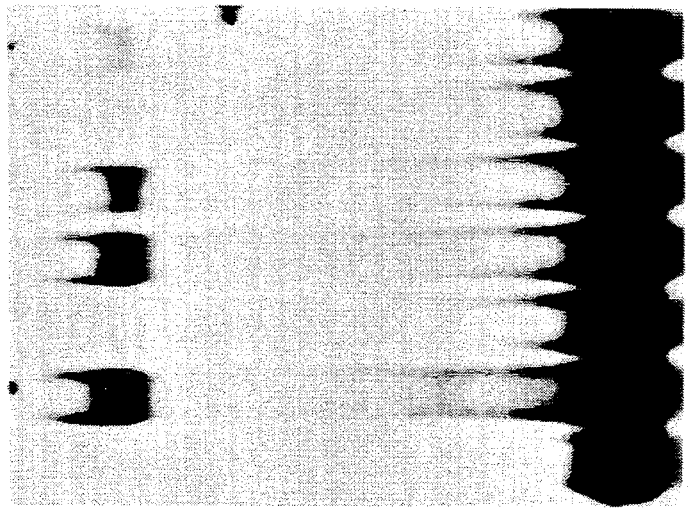
Figure 5A:
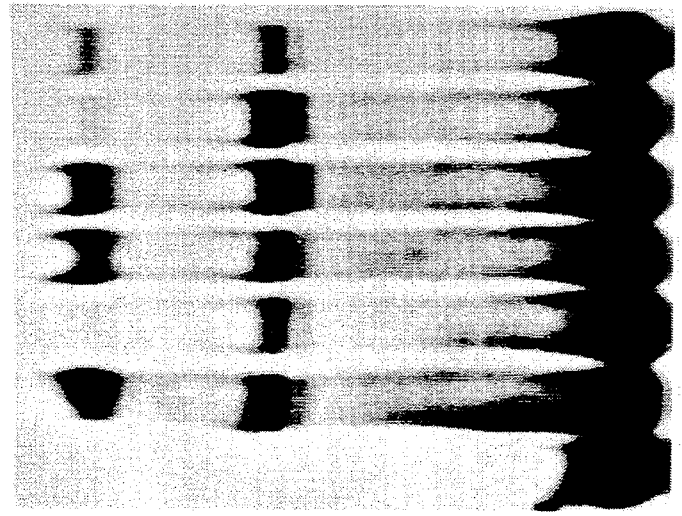
Figure 5C:
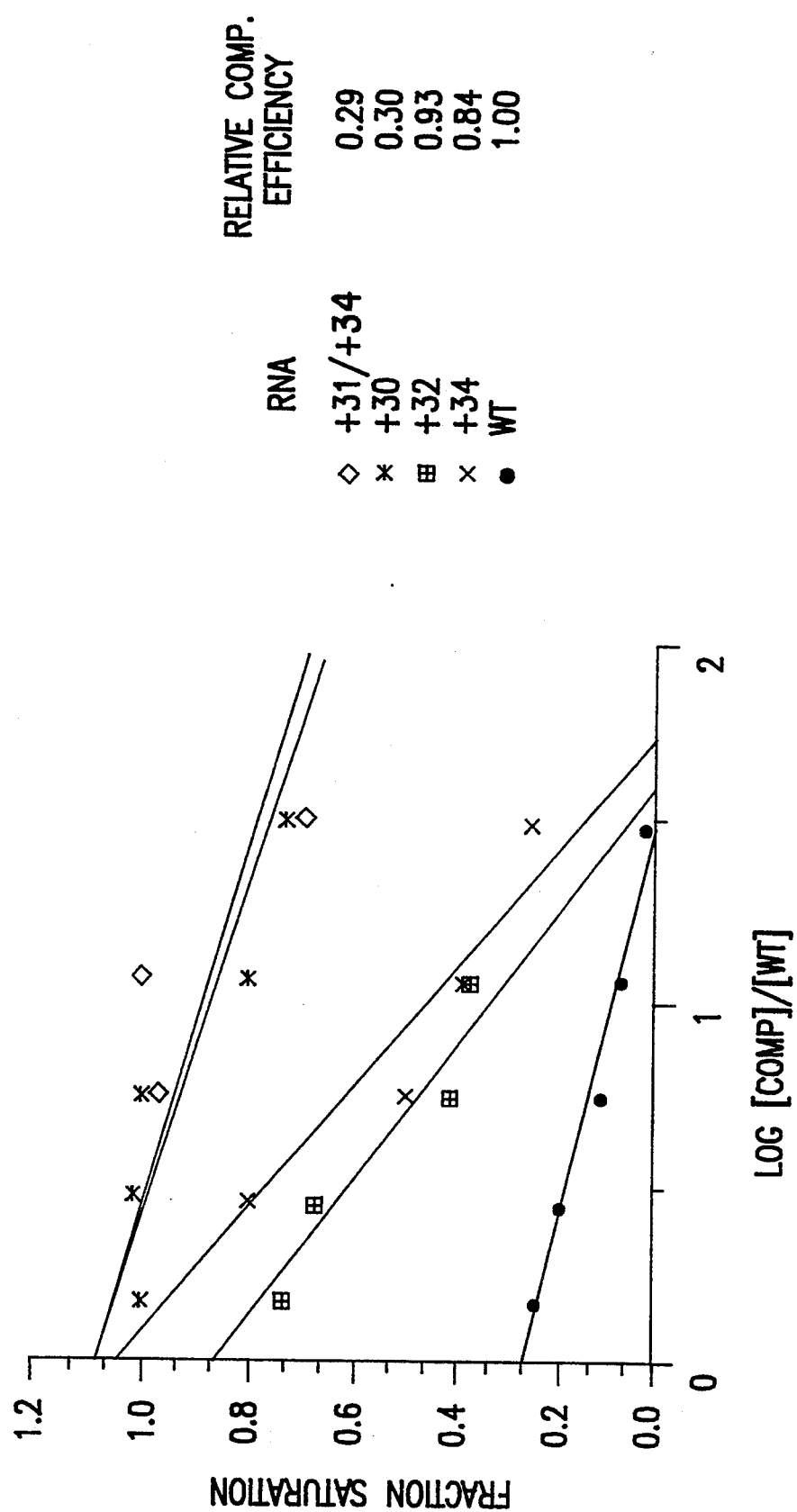

FIGS. 5a-c Competition analysis of TRP-185 and TRP-140 with TAR loop mutants

Gel retardation analysis was performed with internally-labeled wild-type TAR RNA using either hydroxylapatite (FIG. 5A) or analytical sucrose gradient (FIG. 5B) purified TRP-185 with added cofactor. Lanes included probe alone (lane 1), with extract (lane 2), or competition with a 30-fold excess of unlabeled RNA for the wild-type (Lane 3), +31/+34 (Lane 4); +30 (Lane 5); +32 (Lane 6); and +34 (Lane 7). FIG. 5C=Experimental data were plotted, and competition curves and relative competition efficiencies were determined.

FIGS. 6a-d Binding of tat proteins to wild-type and mutant HIV TAR RNA

Both bacterially produced and purified wild-type tat (lanes 1–5) and a mutant tat protein, tat 52/57 (lanes 6–10), were used in gel retardation assays with labeled TAR RNAs corresponding to the wild-type (A), loop substitution mutant +31/+34 (B), bulge point mutant +23 (C), and bulge deletion mutant +23/+25 (D). The amount of tat protein added to each reaction was as follows: 0 (lanes 1, 6), 1.8 ng (lanes 2, 7), 3.6 ng (lanes 3, 8), 7.2 ng (lanes 4, 9), and 14.4 ng (lanes 5, 10).

Figure 7C:
Figure 7B:
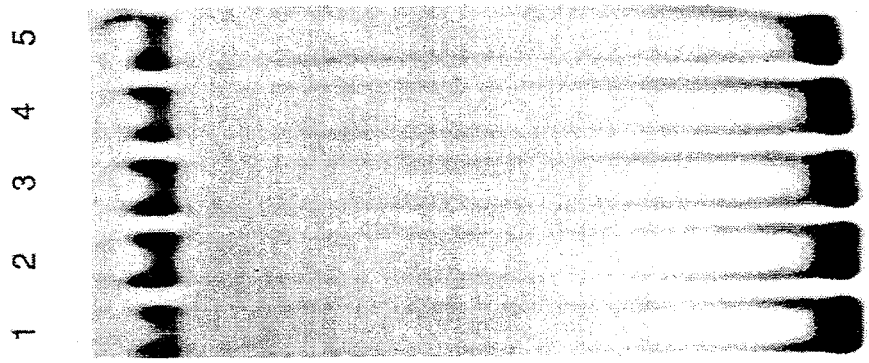
Figure 7A:
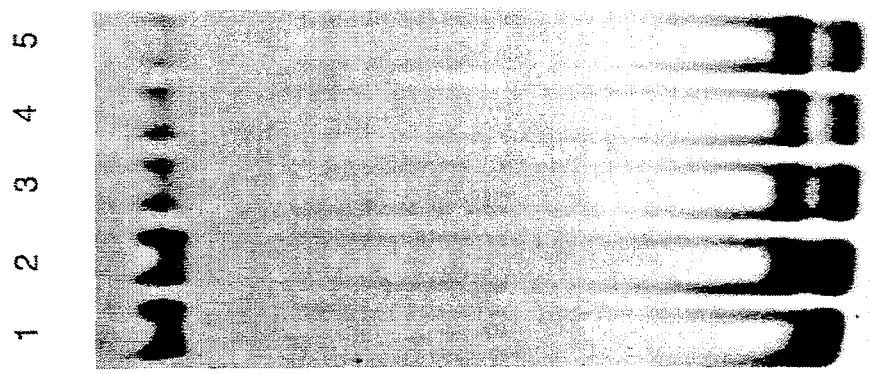

FIGS. 7A, 7B and 7C demonstrate that Tat competes with TRP-185 for binding to TAR RNA TRP-185 and cofactor fractions were used in gel retardation assays with wild-type TAR RNA in the presence of increasing amounts of wild-type tat (A), mutant tat 52/57 (B), or glutathione-S-transferase (GST) (C). In each panel, the amount of added tat or tat 52/57 was 0 (lane 1), 50 ng (lane 2), 200 ng (lane 3), 1000 ng (lane 4) and 3000 ng (lane 5). The amount of GST used (C) was in 20-fold molar excess over corresponding lanes with tat (A) and tat 52/57 (B).

Figure 8:
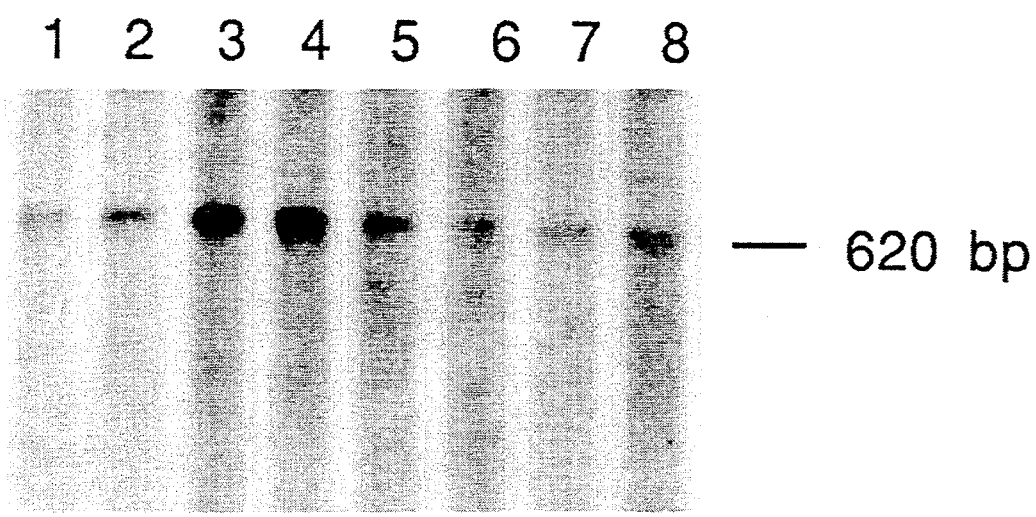

FIG. 8 HIV LTR CAT constructs

A wild-type HIV LTR CAT construct (lanes 1–4) or a similar construct containing a deletion of the TAR bulge region (+23/+25) (lanes 5–8) was restricted with Nco I. HeLa nuclear extract alone (lanes 1 and 5), with the addition of cofactor (lanes 2 and 6), sucrose gradient purified TRP-185 (lanes 3 and 7), or both cofactor and TRP-185 (lanes 4 and 8) were added to each reaction.

Figure 9A:
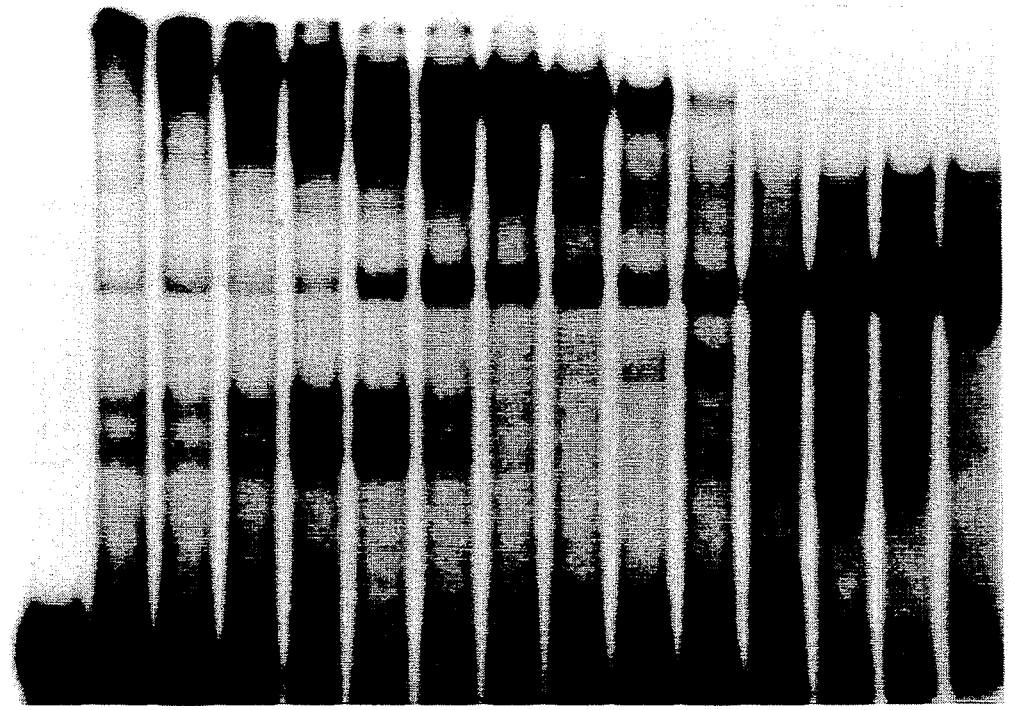
Figure 9B:
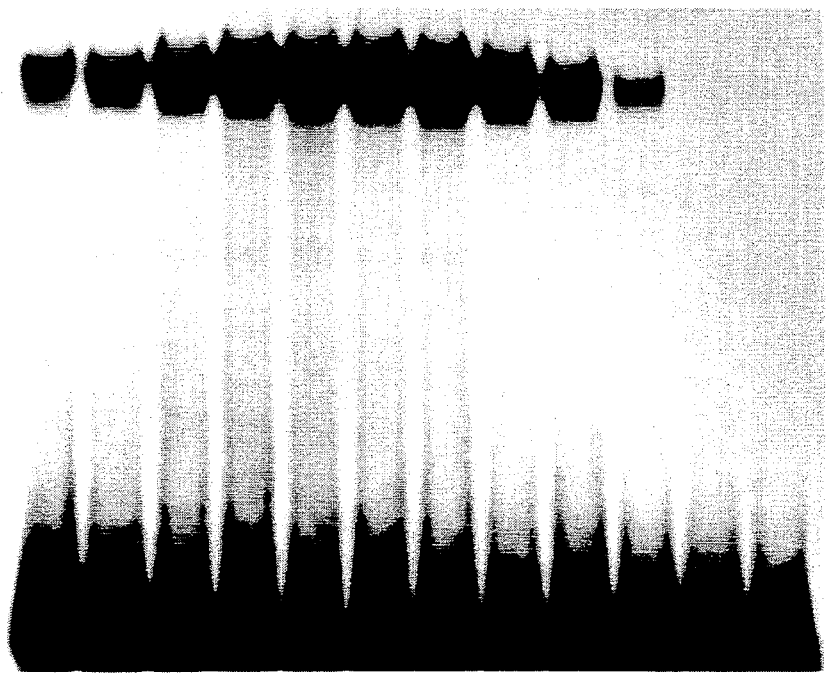

FIGS. 9a and 9b Column chromatography of the purification of TRP-185

FIGS. 9A through 9E illustrate column chromatography of the purification of TRP-185. (A) Superdex 200 FPLC, (B) Bio Rex 70, (C) Dextran blue Sepharose, (D) Mono Q FPLC, (E) sucrose gradients. (B) to (E) column fractions were assayed with the presence of the cofactors fraction. (Activity assay gels are not shown for the first two columns, Heparin agarose and HTP Bio Gel.)

FIG. 10

Silver stain gel of TRP-185 from sucrose gradient fractions.

FIG. 11

Autoradiogram with DNA gel retardation analysis with HIV labeled DNA and competition analysis with cold HIV and adenovirus DNA. The darkest band (lane 1) represents HIV DNA without competition. The next lane (lane 2) represents cold DNA of HIV. Lane 3 represents a mutated HIV DNA. Lane 4 represents the adenovirus DNA.

DETAILED DESCRIPTION OF THE PREFERRED EMBODIMENTS

In its broadest embodiment, the invention provides a cellular protein with nucleic acid binding activity, particularly and most unusually to a viral RNA of HIV. More specifically, the binding protein, designated herein as TRP-185 binds to HIV RNA at a region defined as the TAR region. This TRP-185 cellular protein binds viral RNA. The inventors have observed that the binding activity of the protein for viral RNA for example, may be enhanced in the presence of what is described herein as "cofactor" fraction.

The cofactor fraction includes several peptides. One important peptide in the cofactor fraction is an ~100 kD cofactor. Because the cofactor(s) itself does not bind the RNA, it is believed that the capacity of TRP-185 to bind results from a post-translational modification (i.e., chemical modification) of the TRP-185 (present in the normal cellular environment) by other substances (such as in the "cofactor fraction"). This "modification" may facilitate the binding of TRP-185 to a particular nucleic acid segment binding site on DNA or RNA. For example, with HIV RNA, the substances present in the "cofactor fraction" may act to phosphorylate the TRP-185 protein, thereby facilitating attachment of the "phosphorylated" form of TRP-185 to the TAR region of the HIV RNA. Thus, the binding protein TRP-185 may be employed to regulate the level of gene transcription, and therefore the level of viral activity.

In addition, the present invention also encompasses inhibitors to this protein, (or to the cofactors which are shown to be important to the binding of TRP-185), which may be used to prevent the binding of the TRP-185 protein, to, for example, HIV RNA, and thereby also effect a "turning off" of the HIV virus. By way of example, such an "inhibitor" of TRP-185 could constitute an antibody specific for TRP-185, an antisense DNA, an RNA that preferentially binds the TRP-185 protein or other inhibitors of TRP-185 protein (TAR) binding activity.

The binding protein of the invention may also be regulating cellular genes. While the specific mechanism/function of the protein (TRP-185) in normal cellular gene function is not exactly known, the fact that the protein is cellular and is known to regulate other gene expression (i.e. binding to viral RNA and regulating viral genes) makes probable its role in regulation of cellular genes. The TRP-185 protein may be (in its nonactivated state) sitting on an RNA but be able to move and attach to a variety of DNAs. The TRP-185 protein may thus constitute a critical factor in cellular growth control. Thus, the TRP-185 binding element of the present invention may constitute a reagent useful in the study of nucleic acid binding activity and gene expression, such as HIV regulation and expression.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities and to satisfy "best mode" requirements of the present invention, but should not be construed as limiting the claims thereof.

EXAMPLE 1

Isolation and purification of Nucleic Acid Binding Protein TRP-185

The present example is provided to demonstrate the most preferred method for isolating a bioactive TRP-185 protein from a mammalian nuclear cell extract. However, it is contemplated that upon further sequence analysis of the protein and subsequent cloning and expression of the gene, the TRP-185 binding protein may also be obtained in an even more pure preparation from an expression system (outlined in Example 9). The purification scheme is shown in a flow diagram in Table 1 and is described in detail in this example.

Preparation of Mammalian Nuclear Cell Extract

Virtually any mammalian cell type may be used to prepare the initial nuclear cell extract. By way of example, cell lines which may be used include VERO, Jurkat, CEM, W138, BHK, COS, 293, MDCK, and HeLa cells. Most preferably, the HeLa cell line is the cell line of choice for preparation of the nuclear cell extract.

About 60 liters of HeLa cells were obtained and nuclear extract prepared therefrom. The procedure used was basically that described by Dignam et al. (1983).[35]

Buffers—Buffers used for extract preparation are designated as follows: Buffer W contains 10 mM HEPES (pH 7.9 at 4° C.), 1.5 mM $MgCl_2$, 10 mM KCl and 0.5 mM DTT; Buffer X contains 0.3M HEPES (pH 7.9), 1.4M KCl and 0.03M $MgCl_2$; Buffer Y contains 20 mM HEPES (pH 7.9), 25% (v/v) glycerol, 0.42M NaCl, 1.5 mM $MgCl_2$, 0.2 mM EDTA, 0.5 mM phenylmethylsulfonyl fluoride (PMSF) and 0.5 mM DTT; buffer Z contains 20 mM HEPES (pH 7.9), 20% (v/v) glycerol, 0.1M KCl, 0.2 mM EDTA, 0.5 mM PMSF, and 0.5 mM DTT. DTT and PMSF were added fresh to the buffers just before use.

Cells—HeLa cells ( a line obtained from C. Attardi, California Institute of Technology) were grown in spinner flasks at 37° in Joklik's MEM (minimal essential media) containing 5% calf serum. They were grown to 4 to $6 \times 10^5$ cells per ml prior to harvesting for extract preparation.

Standard Procedure for Extract Preparation—HeLa cells were harvested from cell culture media by centrifugation (at room temperature) for 10 min at 2000 rpm in a Sorvall HG4L rotor. Palette cells were then suspended in five volumes of 4° C. phosphate buffered saline and collected by centrifugation as detailed above; subsequent steps were performed at 4° C. The cells were suspended in five packed cell pellet volumes of buffer W and allowed to stand for 10 min. The cells were collected by centrifugation as before and suspended in two packed cell pellet volumes (volume prior to the initial wash with buffer W) of buffer W and lysed by 10 strokes of a Kontes all glass Dounce homogenizer (B type pestle). The homogenate was checked microscopically for cell lysis and centrifuged for 10 min at 2000 rpm in a Sorvall HG4L rotor pellet nuclei. The supernatant was carefully decanted, mixed with 0.11 volumes of buffer X, and centrifuged for 60 min at 100,000 g $_{av}$ (Beckman Type 42 rotor). The high speed supernatant from this step was dialyzed five to eight hours against 20 volumes of buffer Z and is designated the S-100 fraction.

The nuclear extract was prepared as follows. The pellet obtained from the low speed centrifugation of the homogenate was subjected to a second centrifugation for 20 min at 25,000 g $_{av}$ (Sorvall SS34 rotor), to remove residual cytoplasmic material and this pellet was designated as crude nuclei. These crude nuclei were resuspended in 3 ml of buffer Y per 10$^9$ cells with a Kontes all glass Dounce homogenizer (10 strokes with a type B pestle). The resulting suspension was stirred gently with a magnetic stirring bar for 30 min and then centrifuged for 30 min at 25,000 g $_{av}$ (Sorvall SS34 rotor). The resulting clear supernatant was dialyzed against 50 volumes of buffer Z for five hours. The dialysate was centrifuged at 25,000 g$_{av}$ (Sorvall SS34 rotor) for 20 min and the resulting precipitate discarded. The supernatant, designated the nuclear extract, was frozen as aliquots in liquid nitrogen and stored at −80°. The protein concentration was usually 6 to 8 mg per ml and 15 to 20 mg of protein were obtained from 10$^9$ cells.

Purification of HIV TAR RNA binding protein (TRP-185)

Nuclear extracts were prepared as described above.[35] All procedures were performed at 4° C. Nuclear extract prepared from 60 liters of Hela cells was applied to a heparin-agarose column (2.5×9 cm) and equilibrated with buffer A (20 mM Tris, pH 7.9, 20% glycerol (v/v), 0.2 mM EDTA) containing 0.1M KCl, 0.5 mM DTT and 0.5 mM PMSF. The column was washed with the same buffer until the A$_{280}$ was almost zero, and then bound proteins were eluted with buffer A with 0.4M KCl, 0.5 mM PMSF and 0.5 mM DTT. The 0.4M KCl buffer a fractions were pooled and dialyzed vs. buffer A with 0.1M KCl, 0.5 mM PMSF and 0.5 mM DTT. The dialyzed fraction was then applied to HTP Bio Gel (2.5×5 cm) equilibrated with the same buffer. The column was washed and eluted with buffer A containing 0.1M potassium phosphate. The active fractions were pooled and precipitated with 70% ammonium sulfate and then applied to Superdex 200 FPLC column equilibrated with buffer A containing 0.1M KCL and 1 mM DTT. The active fractions were pooled and applied to a Bio Rex 70 (1.5×3 cm) column in the same buffer. The active flow-through fractions were pooled and applied to Dextran Blue Sepharose (1.5×2 cm) column equilibrated in the same buffer. The column was washed and eluted with buffer A containing 0.4M KCL and 1 mM DTT. The active fractions were pooled and dialyzed vs. Buffer A with 0.1M KCL and 1 mM DTT. The pooled and dialyzed fraction was then applied to Mono Q FPLC 1 ml column equilibrated in the same buffer. The column was washed and eluted with buffer A with 0.4 M KCL. The active fractions were dialyzed vs. 20 mM Tris, pH 7.9, 5% glycerol and 0.2 mM EDTA, 0.1M KCL and 1 mM DTT. These fractions were then loaded onto tubes (1.4×8.9 cm) containing 10 ml of a 5% to 20% continuous sucrose gradient. A preparative sucrose gradient was then performed using Beckman SW 41 Ti rotor at 28,000 rpm for 40 hours at 4° C. The sucrose gradients were fractionated from the bottom of each tube, assayed, and stored at 4° C. At this stage the degree of purification of the TRP-185 protein was approximately 3000-fold. The dissociation constant K$_d$ was determined, and Scatchard analysis for TRP-185 was obtained as described.[41]

A protocol which included less steps in the purification of the nuclear extract and column chromatography over Sephacryl S-300 resulted in poor yield and a less pure preparation of the nucleic acid binding protein. Using that protocol, the partial purification of TRP-185 binding protein obtained was about a 72-fold purified preparation, (see Table 2, final specific activity of 252 ng/mg/+initial activity of 3.5 ng/mg).

The mammalian cell nuclear extract processing protocol outlined in Table 1 is therefor submitted for "best mode" purposes (providing a 1,000–10,000 fold purified TRP-185 protein preparation). However, the TRP-185 nucleic acid binding protein preparations should be equally effacious in, for example, stimulation of HIV gene expression, in analysis by gel retardation and UV cross-linking for binding to TAR RNA, and in the interaction of TRP-185 with TAR RNA in the presence or absence of a "cofactor" fraction. The differences observed between the two preparations, therefore, would only relate to the potency of the TRP-185 preparation.

Prepared according to the above described method, the cellular binding protein TRP-185 may remain stable for between 3-6 months stored at between 0°-4° C.

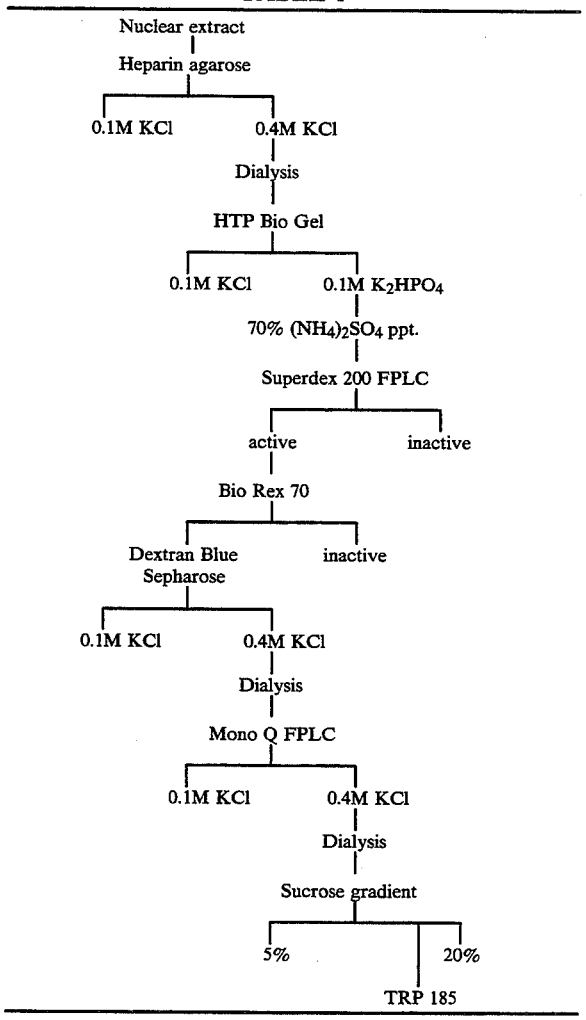

TABLE 1

TABLE 2

| Partial Purification of TRP-185 | | | | | |
|---|---|---|---|---|---|
| Procedure | Volume (ml) | Total Protein (mg) | Total binding activity (ng) | Sp. act* (ng/mg) | Yield (%) |
| HeLa Cells (60 g) | 60 | 3000 | | | |
| Nuclear extract | 60 | 590 | | | |
| Heparin-agarose | 66 | 300 | 1050 | 3.5 | 100 |
| Ammonium Sulfate (ppt.) | 4.9 | 252 | 932 | 3.7 | 89 |

TABLE 2-continued

Partial Purification of TRP-185

| Procedure | Volume (ml) | Total Protein (mg) | Total binding activity (ng) | Sp. act* (ng/mg) | Yield (%) |
|---|---|---|---|---|---|
| Sephacryl S-300 | 40 | 33 | 370 | 11.2 | 35 |
| FPLC Mono S | 35 | 14 | 342 | 24.4 | 33 |
| HTP Bio gel | 5.6 | 3.6 | 168 | 46.8 | 16 |
| Sucrose gradient | 10 | 0.61 | 154 | 252 | 15 |

Maximal binding conditions at each step were determined and then binding was performed at optimal conditions. Appropriate bands were cut out and counted by liquid scintillation.
*Specific activity is defined as the ng of labelled (+1/+80) HIV wt RNA bound per mg of protein in the binding reaction.

While an about 72% fold purified preparation of TRP-185 cellular protein from a HeLa cell extract was obtained using the procedure outlined in Table 2, the modified protocol described herein, which most notably excludes the Sephacryl S-300 column, provided a preparation of about 3,000-fold purity from the HeLa cell nuclear extract.

Gel retardation assay for TRP and tat binding

The probe for binding assay was prepared by in vitro transcription of a plasmid directing the synthesis of nucleotides +1 to +80 from the ARV-2 HIV LTR using T7 polymerase and alpha$^{32}$P-GTP (3000 Ci/mmol). The transcribed RNA was gel-isolated, eluted and used for binding. Approximately 1.5 ng of TAR RNA probe was mixed with extract (0.6 μg–10 μg), poly (I)-poly (C)(0.5 μg–4 μg), and final concentration of 10 mM Tris (pH 7.4), 0.1 mM EDTA, 50 mM KCL, 1 mM 2-mercaptoethanol and 10% glycerol in 50 μl total volume. Protein samples from the heparin-agarose column (10 μg), S 300 column (4 μg), Mono S column (3.9 μg), HTP Bio gel column (2.6 μg) and sucrose gradient pool (0.6 μg) were used. The binding was performed at room temperature for 30 minutes and then the samples were loaded onto a 4% polyacrylamide gel containing 1×TBE and 2% glycerol, and electrophoresed at 180 V in 1×TBE and 2% glycerol at room temperature. The gel was dried and exposed overnight with an intensity screen at 70° C. For sucrose gradient fractions, 10 μl of the cofactor fraction was added to restore activity. For competition analysis, 0–50 ng of each of the unlabeled in vitro transcribed competitor RNAs was mixed with probe and then binding was performed. Binding assays to labeled TAR RNA probes (1.5 ng) were performed in a 50 μl total volume as described (Roy et al., 1990b). Competition experiments with TRP-185 (0.6 μg), cofactor fraction (10 μl) and tat protein (0 to 60 ng) were performed under the same conditions.

UV Crosslinking of TRP-185 to TAR RNA

UV crosslinking of TRP-185 TAR RNA was performed under similar binding conditions. Briefly, the binding reaction of TRP-185 was first done as described above. After 30 minutes at room temperature, the reactions were irradiated under Fotodyne U.V. lamp (maximum emission wavelength 7000 uW/cm2) at a distance of 4.5 cm from the UV source for 30 minutes. 50 U of RNase T1 was added, incubated at room temperature for 10 minutes, loading dye added, heated for 5 minutes at 95° C., and the samples electrophoresed on 8% SDS-polyacrylamide gel. Gels were dried and subject to autoradiography TRP-185 and TRP-140 bind to TAR RNA The purification table for HeLa cell nuclear extracts containing proteins that bound to TAR RNA is indicated in Table 2. Gel retardation analysis was performed to assay different column fractions for their ability to bind TAR RNA. As shown in FIG. 1A, lane 2, one major gel-retarded species was detected following fractionation on heparin agarose. Gel-retardation analysis with unfractionated nuclear extract yielded a number of additional retarded species, but competition analysis indicated that they bound to a variety of non-specific RNA templates (data not shown). Further chromatography on Sephacryl S-300, Mono S fast protein liquid chromatography (FPLC), and hydroxyapatite columns revealed two major gel-retarded species (FIG. 1A, lanes 3–5). These two species could be separated following preparative sucrose gradient centrifugation (FIG. 1A, lanes 6–8).

UV cross-linking in the absence of RNase with each of the column fractions shown in FIG. 1A was also performed (FIG. 1B). The results were consistent with the slower-mobility gel-retarded species migrating on SDS-polyacrylamide gels at 200 kD and the faster-mobility gel-retarded species migrating at 155 kD (FIG. 1B). Treatment of each of these species with RNase T1 following UV cross-linking revealed a decrease in their molecular masses to 185 kD (TRP-185)(FIG. 1C) and 140 kD (TRP-140)(data not shown), respectively. UV cross-linking, gel electrophoresis, and autoradiography of the gel slice containing these gel-retarded species also revealed the presence of either the 185-kD or the 140-kD species (data not shown). It was noted that in the absence of RNase T1, UV cross-linking of wild-type TAR RNA and TRP-185 resulted in two species, whereas in the presence of RNase, only one species was detected (FIG. 1C). It is thus possible that TRP-185 was capable of binding more than one TAR RNA molecule.

Figure 10:
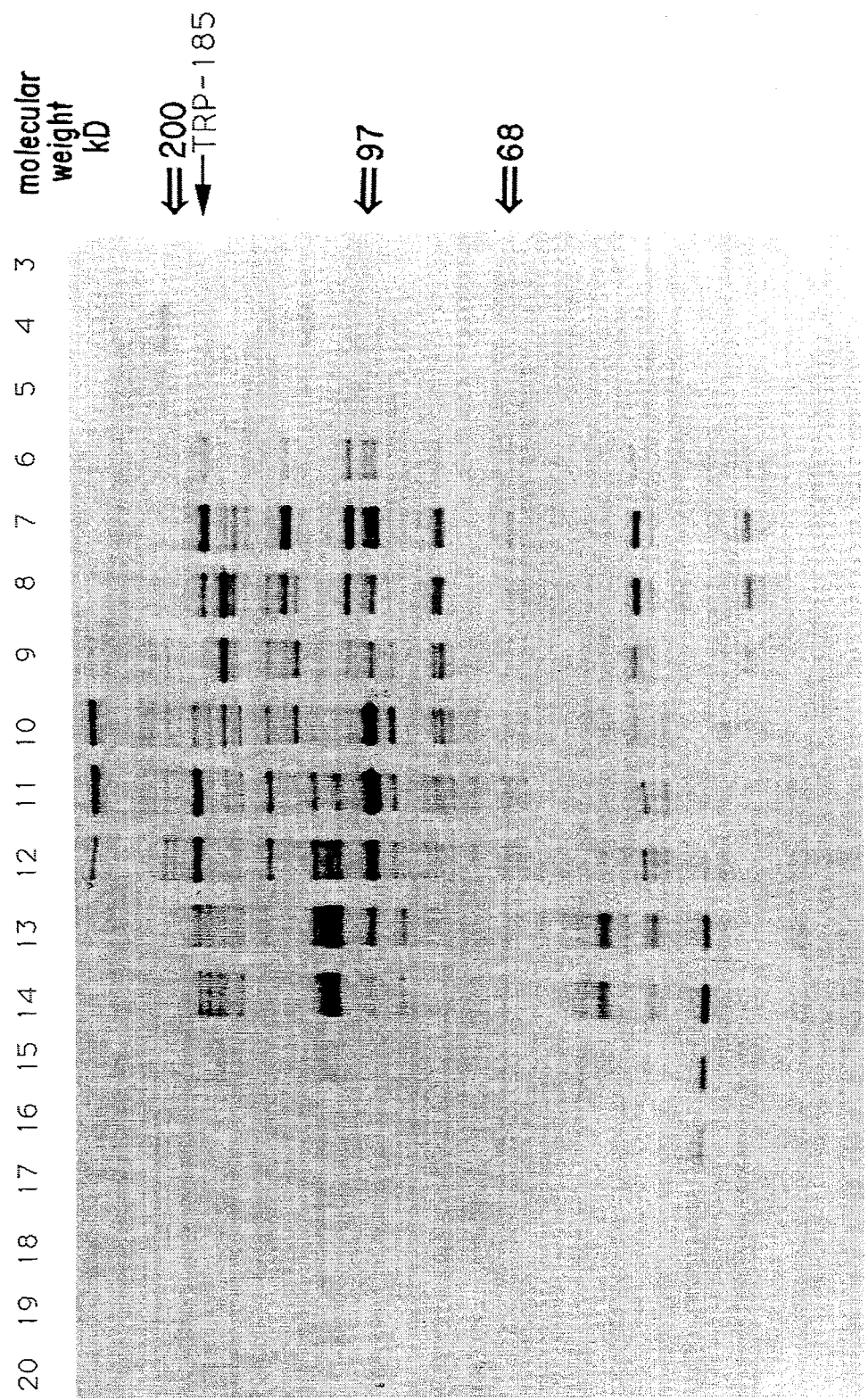

FIG. 9 shows autoradiograms of the last five purification steps in the improved isolation of TRP-185 (Table 1) and FIG. 10 demonstrates a silver stained gel of the TRP-185 sucrose gradient fractions. Fractions 6, 7 and 8 in FIG. 9E correspond to lanes 6, 7 and 8 of the silver stained gel in FIG. 10.

EXAMPLE 2

Preparation and Characterization of a Cofactor Fraction

The present example is provided to teach the method by which the cofactor faction used in the present invention was prepared. The cofactor fraction has been characterized to include several individual cofactors, such as a 100 kD, a 64 kD, and a 46 kD cofactor. The addition of a volume of the entire cofactor fraction must be present to observe binding of TRP-185 to TAR RNA in vitro. Isolated individual cofactors have not been observed to bind to the TAR region of HIV RNA.

Preparation of Cofactor Fraction

Cofactor proteins modulate TRP-185 binding to TAR RNA

Figure 2A:
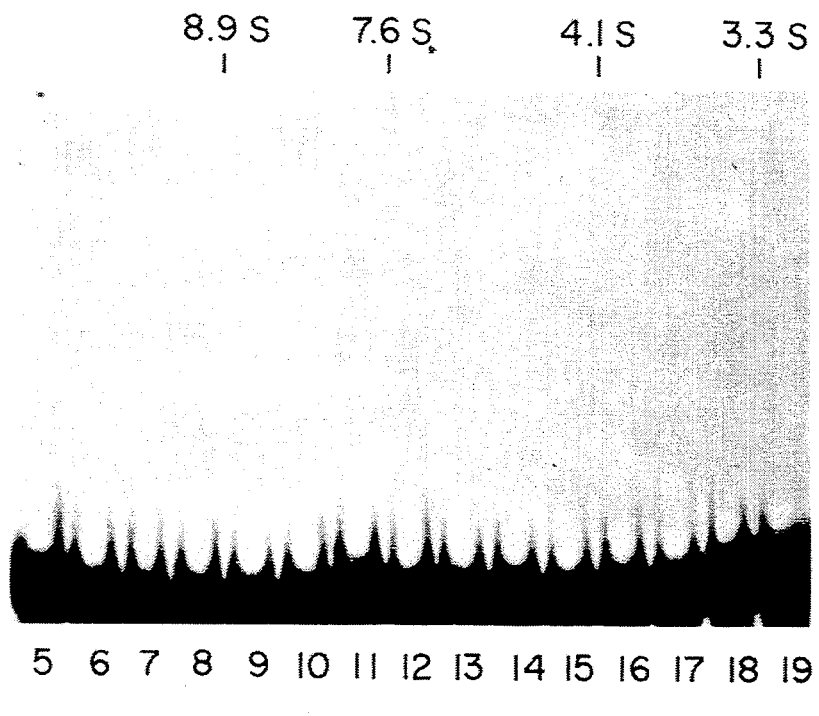
FIGS. 2a and 2b Analytical sucrose gradient analysis of TRP-185.

To determine the binding properties and the native size of TRP-185, preparative sucrose gradient fractions containing TRP-185 were further characterized by analytical sucrose gradient centrifugation (FIG. 2). Molecular weight markers were included in parallel gradients to determine the position of TRP-185 in the gradient. None of the fractions from the analytical sucrose gradient including fractions that contained proteins migrating between 180–200 kDa gave rise to gel-retarded species (FIG. 2A). Prolonged exposures of this autoradiogram did not result in detectable gel-retarded species (data not shown). This suggested that TRP-185 may require several components for binding to TAR RNA as previously suggested (FIG. 1A, lines 7-9).

Figure 2B:
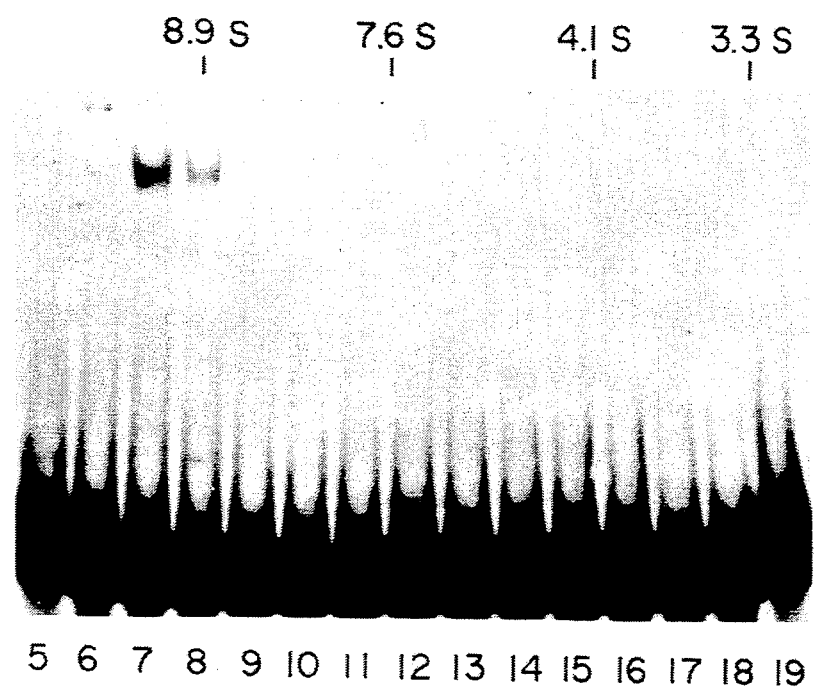

Individual fractions from the original preparative sucrose gradient (see Example 1) were added to fractions from the analytical sucrose gradient. The combined fractions were then analyzed by gel retardation analysis (FIG. 2B). Fractions from the analytical sucrose gradient which comigrated at 9.5S (near the 200 kDa molecular weight marker) were active in gel-retardation only when combined with an additional fraction which sedimented at about 100 kDa in the preparative sucrose gradient (FIG. 2B). This 100 kDa cofactor (CF) fraction did not result in UV crosslinked or gel retarded species either alone (FIG. 1A and 1B, lane 9) or when combined with other sucrose gradient fractions. Heat lability, trypsin sensitivity, and further fractionation were consistent with the fact that this cofactor fraction contained proteins. These results were consistent with a model in which the binding activity of TRP-185 is modulated by cofactors which were themselves not capable of binding TAR RNA directly.

It is possible that these cofactors may be a class of cellular kinases which alter the phosphorylation of TRP-185, with resultant changes in its binding affinity. The observation that protein kinase C expression vectors activate tat-mediated expression via the TAR element is consistent with this possibility.[36] However, it cannot definitively be ruled out that TRP-185 may weakly interact with these cofactor species. Similar interactions occur with the multisubunit factor, CstF, which is required for mRNA polyadenylation.[39,40] A 64 kDa species is seen upon UV crosslinking of CstF to RNA, but other components of the complex must be present to reconstitute the binding of this species. Both UV crosslinking and sucrose gradient analysis indicate the TRP has a molecular weight of approximately 185 kDa which makes the presence of a multi-component complex unlikely.

EXAMPLE 3

Preparation of Antibodies to TRP-185 Antigen

Monoclonal and polyclonal antibodies raised against TRP-185 exposed and unexposed to cofactor fraction are obtained as described in this example. These antibodies are useful for (1) screening a cDNA expression library in the process of cloning the gene that encodes TRP-185 (for example, the SUPERSCREEN® immunoscreening system from AMERSHAM®[53]), (2) facilitating the purification of TRP-185 by using column chromatography to which the monoclonal antibody is bound, and (3) providing reagents necessary for a diagnostic immunoassay for screening biological samples.

Monoclonal antibodies are obtained using the following procedure:[51]

Immunization Schedule for Raising Monoclonal Antibodies

1. For each mouse, mix 250 μl of antigen solution containing 10 μg of TRP-185 with 250 μl of complete Freund's adjuvant. Inject six BALB/c female mice ip (intraperitoneal injection).
2. After 14 days, repeat the injections of TRP-185 and incomplete Freund's adjuvant.
3. Collect tail bleeds from immunized mice on day 24. Do 1 in 5 dilutions in phosphate buffered saline (PBS) and test all samples by comparison with similar dilutions of normal mouse serum in a dot blot.
4. On day 35, inject all animals ip with TRP-185 and incomplete Freund's.
5. Day 45, do tail bleeds and test by dot blot. All serum samples checked by immunoprecipitation against in vivo radiolabeled antigen preparation.
6. Day 56, inject best responder, 100 μl iv and 100 μl ip. All others get ip injection with incomplete Freund's.
7. Day 59, fuse splenocytes from best responder.

The resultant hybridoma tissue culture supernatants are screened for monoclonal antibodies as follows:

1. A protein solution of at least 1 μg/ml of TRP-185 is added to a nitrocellulose sheet at 0.1 ml/cm². Allow the protein to bind to the paper for 1 hr. Higher concentrations of proteins will increase the signal and make screening faster and easier. If the amount of protein is not limiting, concentrations of 10–50 μg/ml should be used. Nitrocellulose can bind approximately 100 μg of protein per cm². p1
2. Wash the nitrocellulose sheet three times in PBS.
3. Place the sheet in a solution of 3% BSA in PBS with 0.02% sodium azide for 2 hr to overnight. To store the sheet, wash twice in PBS and place at 4° C. with 0.02% sodium azide. For long-term storage, shake off excessive moisture from the sheet, cover in plastic wrap, and store at −70° C.
4. Place the wet sheet on a piece of parafilm, and rule with a soft lead pencil in 3-mm squares. Cut off enough paper for the number of assays.
5. Apply 1 μl of the hybridoma tissue culture supernatant to each square. Incubate the nitrocellulose sheet on the parafilm at room temperature in a humid atmosphere for 30 min.

Along with dilutions of normal mouse serum, include dilutions of the mouse serum from the last test bleed as controls. Dilutions of the test sera are essential to control correctly for the strength of the positive signals. Mouse sera will often contain numerous antibodies to different regions of the antigen and therefore will give a stronger signal than a monoclonal antibody. Therefore, dilutions need to be used to lower the signal. Good monoclonal antibodies will appear 10-fold less potent than good polyclonal sera.

6. Quickly wash the sheet three times with PBS, then wash two times for 5 min each with PBS.
7. Add 50,000 cpm of $^{125}$I-labeled rabbit anti-mouse immunoglobulin per 3-mm square in 3% BSA/PBS with 0.02% sodium azide (about 2.0 ml/cm²).
8. After 30–60 min of incubation with shaking at room temperature, wash extensively with PBS until counts in the wash buffer approach background levels.
9. Cover in plastic wrap and expose to X-ray film with a screen at −70° C.

The hybridoma identified as producing antibody to TRP-185 exposed and unexposed to cofactor fraction is passaged as follows:

1. Inject 10⁷ (or less) cells into female mice that have been injected ip about 1 week earlier with 0.5 ml of pristane or incomplete Freund's adjuvant. These types of injections are also used to prime mice for ascites production, and this may serve as a convenient source of appropriate hosts. If no mice are available, inject mice with incomplete Freund's adjuvant and wait 4 hr to 1 day before injecting the hybridoma cells. The animals must be of the same genetic background as your cell line.
2. If an ascites develops, tap the fluid and transfer into a sterile centrifuge tube.
3. Spin the ascites at 400 g for 5 min at room temperature.
4. Remove the supernatant. Resuspend the cell pellet in 10 ml of medium supplemented with 10% fetal bovine serum and transfer to a tissue culture plate. The supernatant can be checked for the presence of the antibody and used for further work if needed.
5. Handle as for normal hybridomas, except keep the cells separate from the other cultures until there is little chance of the contamination reappearing.

EXAMPLE 4

Specificity of TRP-185 Binding for HIV TAR RNA

To determine whether TRP-140 and TRP-185 bound specifically to TAR RNA, RNA gel retardation and competition analysis were performed.

Plasmid constructs and labeling of mRNAs

Wild-type and mutant HIV mRNAs were constructed by fusing a synthetic linker containing a T7 RNA polymerase promoter to DNA fragments of the indicated TAR constructs from +1 to +80[10]. Transcription of these constructs was linearized with Hind III (+80) using T7 RNA polymerase resulting in transcripts consisting of nucleotides +1 to +80 of the HIV LTR. RNA synthesis, labeling, and purification were performed using the reagents and procedures of the Riboprobe System II (Promega).[32]

Figure 3A:
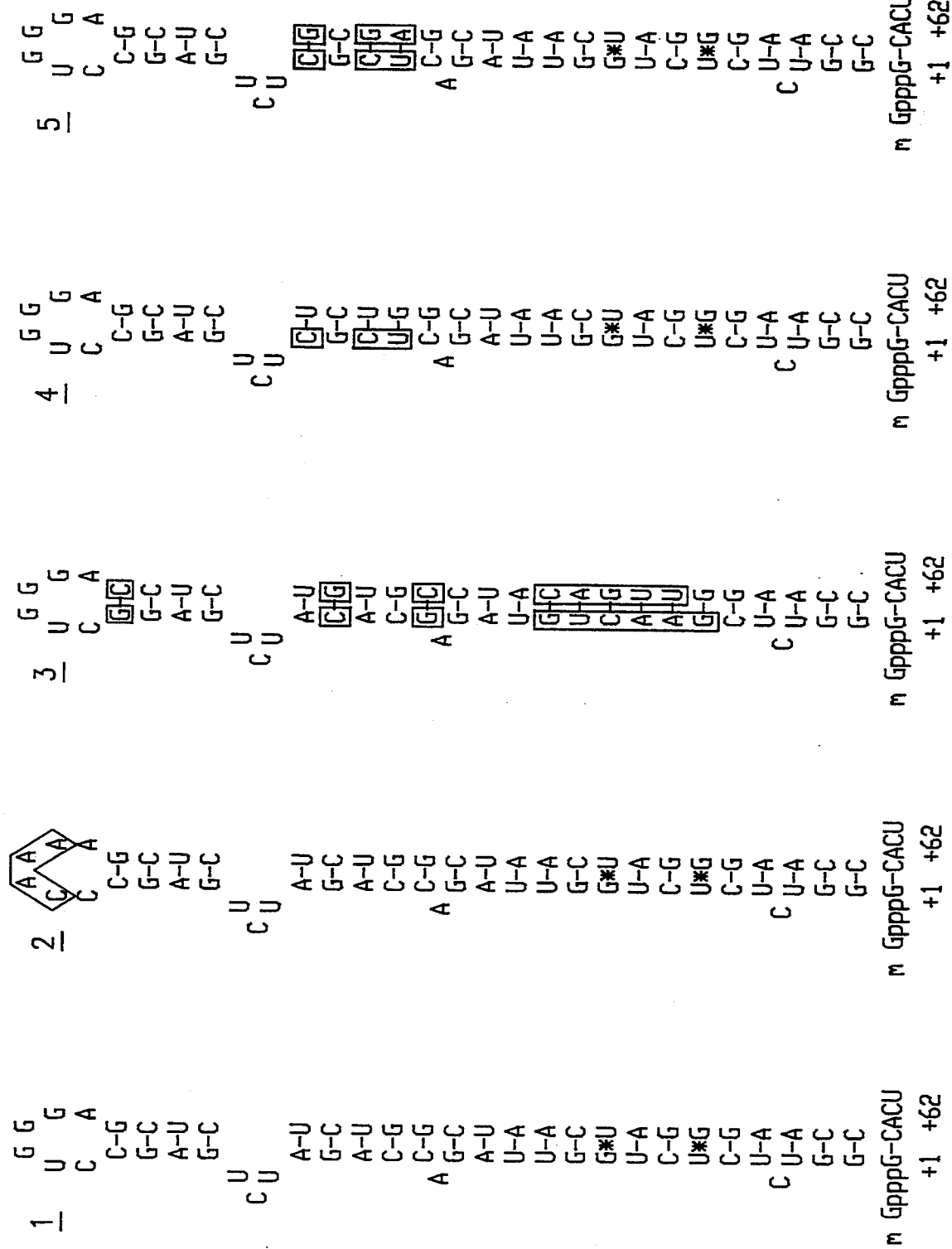
FIGS. 3A and 3B in the HIV TAR region.
Figure 3B:
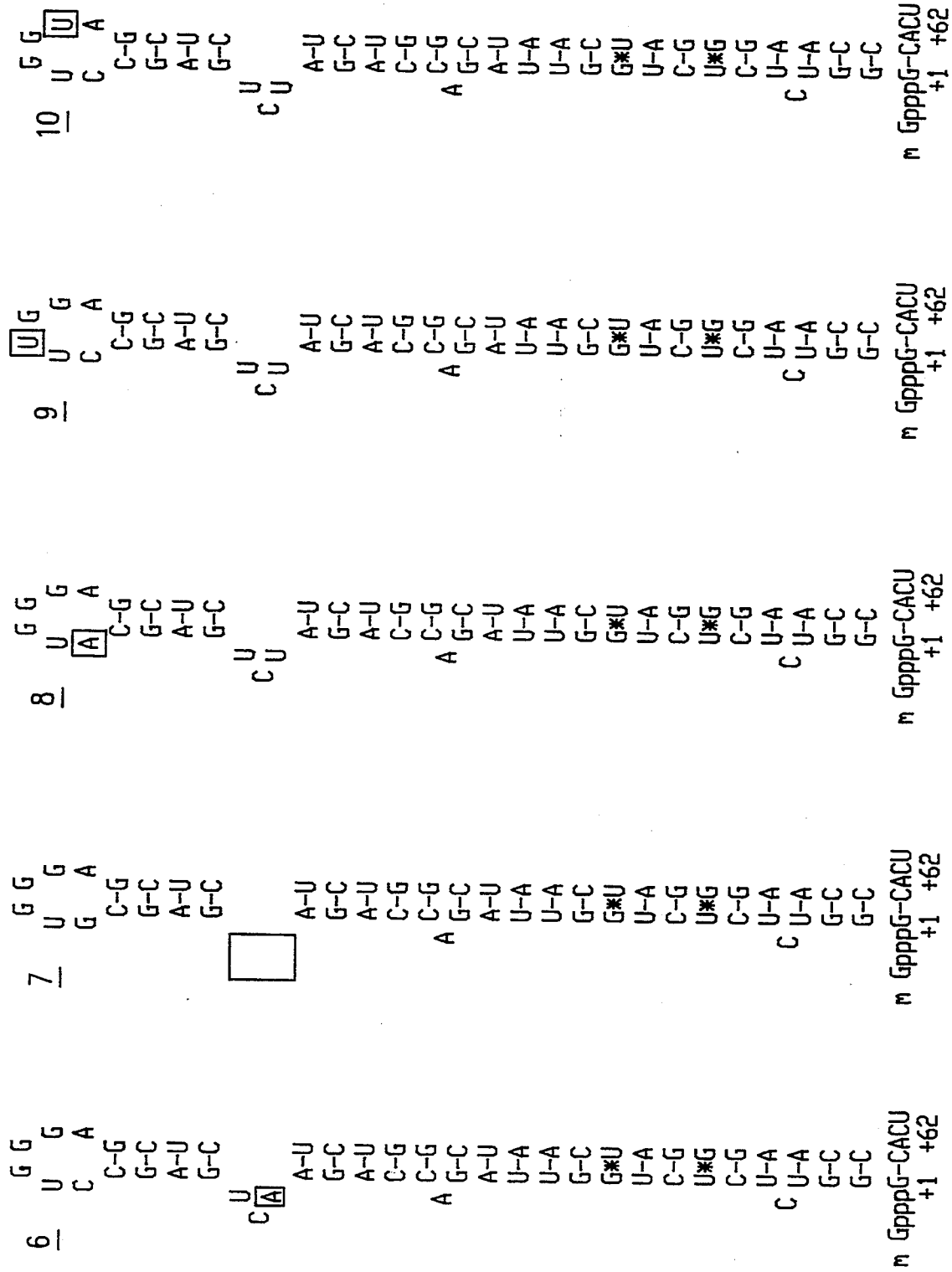

TRP-185 binding requires both the TAR RNA loop sequences and secondary structure Each of the TAR RNA species illustrated in FIG. 3 was placed downstream of the T7 promoter and transcribed in vitro in either the presence or absence of labeled nucleotides. These constructs include wild-type, a substitution of the loop sequences (+31/+34), a mutation of the TAR primary sequence (TAR-sense), a disruption of the stem structure (+19/+22), restoration of the stem structure/(+19/+22)/(+40/+43)/, a point mutation in the bulge region (+23), a deletion of the bulge region Δ(+23/+25), and mutations in the loop sequences at positions (+30), (+32), and (+34). Gel retardation with labeled wild-type TAR RNA and competition with unlabeled RNAs were performed with both TRP-140 and TRP-185 eluted from the hydroxylapatite column, and with TRP-185 plus a cofactor fraction obtained from sucrose gradient centrifugation (FIGS. 4 and 5). Table 3 reveals the relative activity of each of these constructs in the context of the HIV LTR when transfected into HeLa cells in the presence of a tat expression vector. Thus, we could correlate in vitro binding assays with the in vivo activity of these templates.

TABLE 3

| Relative activity of TAR mutant constructs with tat | |
| --- | --- |
| Construct | Relative CAT activity |
| 1. wild-type | 1.0 |
| 2. (+31/+34) | 0.04 |
| 3. TAR sense | 0.41 |
| 4. (+19/+22) | 0.08 |
| 5. (+19/+22)/(+40/+43) | 0.96 |
| 6. (+23) | 0.22 |
| 7. Δ(+23/+25) | 0.25 |
| 8. (+30) | 0.16 |
| 9. (+32) | 0.18 |

TABLE 3-continued

| Relative activity of TAR mutant constructs with tat | |
| --- | --- |
| Construct | Relative CAT activity |
| 10. (+34) | 0.22 |

Transfections of each of these constructs in the context of the HIV LTR (−170/+80) fused to CAT in the presence of a tat expression vector were performed and the percent CAT conversion determined.[43] The results were normalized to the percent CAT conversion of the wild-type construct and reflect the average of three independent experiments.

Gel retardation with the hydroxylapatite column fraction revealed two species corresponding to TRP-140 and TRP-185 (FIG. 4A, lane 2). TRP-185 was competed by a 30-fold excess of unlabeled wild-type TAR RNA while TRP-140 was not competed using a similar amount of competitor (FIG. 4A, lane 3). Larger quantities of wild-type competitor resulted in the loss of TRP-140 binding, but all other TAR RNAs tested also competed at similar concentrations, indicating minimal binding specificity for TRP-140 (data not shown). TAR RNA species containing substitutions of the loop sequences (+31/+34) resulted in only minor levels of competition of TRP-185, indicating a critical role for the loop sequences in TRP-185 binding (FIG. 4A, lane 4). Mutation of the TAR RNA primary sequence (TAR-sense) resulted in levels of competition of TRP-185 similar to that found with wild-type TAR RNA (FIG. 4A, lane 5). A disruption of the TAR stem structure (+19/+22) resulted in decreased competition of TRP-185 binding (FIG. 4A, lane 6), while restoration of the stem structure (+19/+22)/(+40/+43) resulted in near wild-type levels of competition (FIG. 4A, lane 7). A point mutation in the bulge (+23) resulted in near wild-type competition (FIG. 4A, lane 8), but a deletion of the entire bulge region Δ(+23/+25) resulted in minimal competition being nearly as defective as the loop mutant (+31/+34) (FIG. 4A, lane 9). A similar series of gel retardation and competition, assays for TRP-185 was performed using sucrose gradient isolated TRP-185 and cofactor containing fractions (FIG. 4B). The pattern of competition for TRP-185 was similar to that seen using fractions from the hydroxylapatite column (FIG. 4B). This indicated that TRP-140 was not required for the binding properties of TRP-185. Competition curves and relative competition efficiencies for each of these constructs are shown in FIG. 4C.

Since the loop sequences appeared critical for the binding of TRP-185, we used both hydroxylapatite and sucrose gradient fractions containing TRP-185 in gel retardation and competition analyses with wild-type TAR RNA and several loop point mutants (FIGS. 5A and 5B). With the hydroxylapatite column fractions, the wild-type TAR RNA again resulted in marked competition for TRP-185 binding (FIG. 5A, lane 3) while the loop substitution mutant (+31/+34) resulted in only minimal competition (FIG. 5A, lane 4). Mutation of nucleotide (+30) in the loop resulted in only slight competition of TRP-185 binding, similar to the results obtained with the (+31/+34) loop substitution mutant, indicating the importance of this nucleotide in the loop for TRP-185 binding (FIG. 5A, lane 5). Mutation of nucleotide (+32) in the loop resulted in significant levels of competition of TRP-185 binding (FIG. 5A, lane 6) though less than was seen with wild-type TAR RNA while mutation of nucleotide (+34) resulted in intermediate levels of competition for TRP-185 binding (FIG. 5A, lane 7). None of these RNAs containing point mutations in the loop region resulted in significant competition for TRP-140 at the concentrations tested (FIG. 5A). Similar results were seen with sucrose gradient purified TRP-185 (FIG. 5B). Competition curves and relative competition efficiencies for each of these constructs are shown in FIG. 5C.

The results indicated that individual nucleotides in the loop region were critical for TRP-185 binding, but different nucleotides had somewhat variable effects on its binding. Though a point mutation in the bulge did not greatly alter TRP-185 binding, a deletion of the bulge resulted in marked decreases in its binding. In addition to determining regions of TAR RNA required for efficient TRP-185 binding, the binding affinity of TRP-185 was also calculated. The binding affinity ($K_d$) of TRP-185 to TAR RNA was calculated to be $3.15 \times 10^{-5}$M while its affinity to nonspecific RNA was $2.11 \times 10^{-5}$M (data not shown). Thus TRP-185 bound to TAR RNA with both high affinity and marked specificity.

EXAMPLE 5

RNA Gel Retardation Analysis and Competition Analysis of TRP-185 Binding

The present example is provided to demonstrate the competition between tat and TRP-185 for binding to the TAR RNA loop sequence. The particular protocols employed to demonstrate this competitive binding are (1) RNA gel retardation, and (2) competition analysis with tat protein.

For tat bacterial expression, DNA fragments encoding either wild type tat or tat 52/57[45] which contains the amino acids Gly Gly Ala Gly Gly Gly in place of the native amino acids Arg Arg Gln Arg Arg Arg (amino acids 52–57) were used. By changing the sequence GAAATG encompassing the initiating methionine to AGATCT, a BglIII/EcoRI fragment of a tat subclone containing the second exon of tat was cloned into pGEX-2T (Smith and Johnson, 1988). Following cleavage with thrombin at the recognition motif between the GST-tat junction, tat proteins were generated and purified which consisted of amino acids 2 to 72 of tat preceded by Arg-Ser contributed by the BglIII sequence.

Purification of bacterial synthesized tat protein

Overnight cultures of wild-type or mutant tat(52/57) in pGEX-2T were diluted 1/100 in 500ml of fresh medium and grown to an O.D. of 0.6 at 37° C. The tat fusion proteins were induced by the addition of IPTG to a final concentration of 0.1 mM. Cultures were grown for four additional hours, the pellets harvested, and resuspended in 5 ml of 1×PBS (150 mM NaCl, 16 mM Na$_2$HPO$_4$, 4 mM NaH$_2$PO$_4$, pH 7.3) plus 0.5 mM PMSF and 1 mM DTT. Cells were lysed on ice by sonication, spun at 12,000 rpm for 15 min., and loaded on a 1 ml glutathione-Sepharose affinity column (Smith and Johnson, 1988). The column was washed with the above buffer and eluted with buffer containing 50 mM Tris (pH 8.0), 1 mM DTT and 5 mM glutathione. Fractions containing the tat fusion proteins were pooled, extensively dialyzed against PBS with 1 mM DTT, and loaded for a second passage on a glutathione-sepharose column. The column was washed with five column volumes of PBS with 1 mM DTT, five column volumes of buffer containing 50 mM Tris (pH 8.0), 150 mM NaCl, 2.5 mM CaCl$_2$, and 1 mM DTT, and then incubated with the same buffer and 6 μg of human thrombin (Sigma) for 40 min at room temperature with mixing. The flow through fractions which contained thrombin-released tat were collected and extensively dialyzed against 20 mM Tris (pH 7.9), 0.2 mM EDTA, 100 mM KCl, 20% glycerol, 1 mM DTT and 0.5 mM PMSF, then stored at −70° C.

Following dialysis to remove the CaCl$_2$ and after the addition of PMSF, no residual thrombin activity in tat preparations was demonstrated as judged by assays with other proteins containing thrombin recognition motifs. The presence of tat was confirmed by Western analysis with tat antisera (Pearson et al, 1990) and Coomassie staining of polyacrylamide SDS gels. The dissociation constants ($K_d$) and Scatchard analysis for tat binding to the TAR RNA wild-type and loop mutants were determined as described (Baker et al., 1986).

Characterization of Wild-Type and Mutant tat Protein Binding to TAR RNA Templates In the described studies, it was established that tat regulated the binding of TRP-185 to TAR RNA. The possibilities that we addressed were whether both tat and TRP-185 bound simultaneously to TAR RNA or whether these proteins competed for binding to the TAR RNA. Both wild-type tat and a tat mutant (tat 52/57), which substituted six neutral amino acids (glycine and alanine) in the basic domain of tat between amino acids 52 and 57,[45] were produced as fusion proteins with glutathione S-transferase using the procaryotic expression vector pGEX.[48] These tat fusion proteins were purified by multiple passages on glutathione agarose affinity columns. Authentic tat proteins were liberated by removal of the glutathione S-transferase moiety following cleavage with thrombin at a recognition site engineered into the fusion protein. Both wild-type tat and tat 52/57 were judged to be greater than 95% pure and each preparation yielded a single species of approximately 9 kDa following gel electrophoresis and Coomasie staining. The purification of wild-type tat protein under these conditions eliminated harsh elution and denaturation procedures used in several other purification schemes, resulting in both a higher binding affinity and binding activity for TAR RNA than previously reported.[16,28]

To first characterize the binding properties of these tat proteins, gel retardation analysis was performed with labeled TAR RNA derived from either wild-type, a loop mutant (+31/+34), a bulge point mutant (+23), or a bulge deletion mutant (+23/+25) (FIG. 6). All TAR RNA probes were labeled to the same specific activity. The wild-type tat protein bound to wild-type TAR RNA with a $K_d$ of $6.4 \times 10^{-10}$M. Scatchard analysis indicated that one tat molecule bound to each TAR RNA molecule and that all the binding sites of tat were active (FIG. 6A, lanes 1–5). tat 52–57 bound poorly to wild-type TAR. RNA due to the fact that the majority of basic amino acids in the basic domain were substituted with neutral amino acids (FIG. 6A, lanes 6–10). These results were consistent with previous results, implicating the basic domain in tat for binding to TAR RNA.[16,30,49]

Figure 6A:
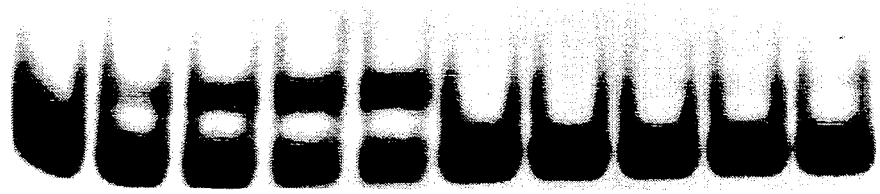
Figure 6B:
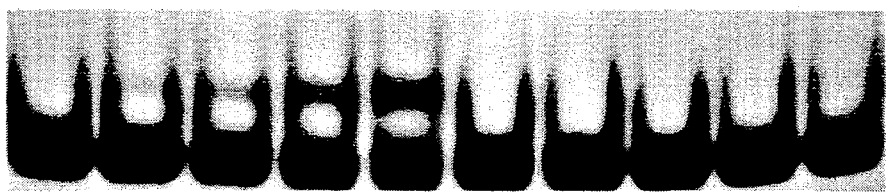
Figure 6C:
Figure 6D:
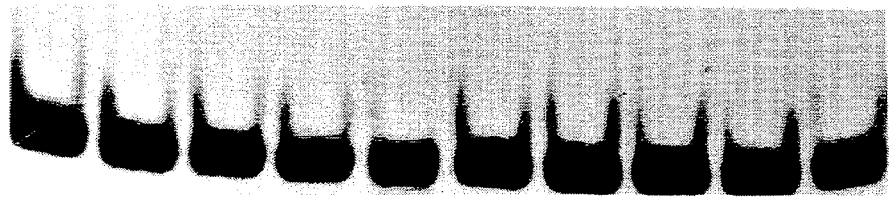

Next we tested the binding of these tat proteins to the TAR RNA loop substitution mutant (+31/+34). The wild-type tat protein bound to this TAR RNA mutant with five-fold lower affinity than to wild-type TAR RNA (FIG. 6B, lanes 1–5). Similar results have previously been noted using tat peptides in gel retardation analysis with a similar TAR RNA loop mutant.[49] tat 52/57 did not bind to this template (FIG. 6B, lanes 6–10). TAR RNA containing either a point mutation in the bulge at (+23)(FIG. 6C, lanes 1–10) or a deletion of the bulge region (+23/+25) (FIG. 6D, lanes 1–10) did not result in detectable binding of either wild-type tat or tat 52/57. These results were consistent with previous studies which indicated a predominant role for the bulge region in tat binding,[16,28,30,49] but also suggested that wild-type loop sequences influenced the affinity of tat binding to TAR RNA.

Tat competes with TRP-185 for binding to TAR RNA

TRP-185 was demonstrated to require an intact TAR RNA stem and bulge structure and wild-type loop sequences for efficient binding. Next we determined whether the addition of either wild-type tat or tat 52/57 influenced the binding of TRP-185 to TAR RNA. Gel retardation analysis was performed with a constant amount of TRP-185 and increasing amounts of wild-type tat protein added to labeled wild-type TAR RNA. As increasing amounts of tat bound to the TAR RNA, there was decreased binding of TRP-185 to the TAR RNA (FIG. 7A, lanes 1-5). No evidence for simultaneous binding of both tat and TRP-185 to TAR RNA was noted. This result suggested that tat was able to complete with TRP-185 for binding to TAR RNA. This result was further substantiated by gel retardation with wild-type TAR RNA using similar amounts of tat 52/57 and TRP-185. This tat mutant, which was unable to bind efficiently to TAR RNA, did not reduce the binding of TRP-185 to TAR RNA (FIG. 7B, lanes 1-5). The addition of purified glutathione S-transferase protein obtained during the tat purification also did not decrease the binding of TRP-185 to TAR RNA (FIG. 7C, lanes 1-5). Finally, the wild-type tat protein did not decrease the binding of TRP-185 when a TAR RNA bulge point mutant template (+23) was used in gel retardation analysis (data not shown). These results suggested that tat competed with TRP-185 for binding to TAR RNA.

A direct interaction between TRP-185 and tat which is independent of TAR RNA is possible. Due to the proximity of the bulge and loop regions and the fact that the binding affinity for both of these proteins is similar (between $3 \times 10^{-10}$ and $6 \times 10^{-10}$), stearic effects may be responsible for the fact that only tat or TRP-185 can bind in vitro to each TAR RNA template. However, we cannot rule out that high affinity binding of tat to TAR RNA requires the loop sequences in addition to the bulge region and this binding of tat to the loop sequences could potentially inhibit TRP-185 binding. Mutations in the upper portion of TAR RNA including the loop or bulge regions may dramatically influence TAR RNA structure with subsequent effects on the ability of both cellular and viral proteins to bind to TAR RNA. Thus, the in vivo phenotype of the TAR RNA loop and bulge mutations may be due to decreased binding of either TRP-185 and/or tat.

EXAMPLE 6

TRP-185 Stimulation of HIV Gene Expression

The present example demonstrates that TRP-185 stimulates gene expression from a wild-type HIV-LTR template. However, no stimulation of gene expression from an HIV template containing mutations in TAR was shown. These results indicate TRP-185 is a cellular factor that is regulated by the tat protein and which is involved in modulating the level of HIV gene expression.

In vitro transcription of the HIV LTR

HIV constructs in pJGFCAT18 extending from −179 to +80 were restricted with NcoI to generate a 620 bp run-off transcript. The TAR-antisense construct (Garcia et al. 1989) was restricted with EcoRI to generate a 290 bp run-off transcript. Transcription reactions were performed in 10 mM Hepes, pH 7.9, 10 mM Tris (pH 7.9), 10% glycerol, 50 mM KCl, 0.1 mM EDTA, 1 mM DTT, 5 mM MgCl$_2$, 10 mM creatine phosphate, 0.5 μg of poly (I)-poly (C), and 600 mM each of ATP, CTP, UTP, 40 μM GTP, and 1μ of [$\alpha^{32}$P] GTP (3000 Ci/m mole). HeLa nuclear extract (Dignam et al., 1983)(100 μg) was included in each reaction and incubated at 30° C. for 1 hr. The final α-amanitin concentration was 2.0 μg/ml where indicated. Either 0.6 μg of TRP-185 fraction from a sucrose gradient preparation or 10 μl of cofactor fractions was included to determine the effects of TRP-185 on activation of the HIV LTR. All reactions were stopped by the addition of 400 μl of 7M urea, 0.35M NaCl, 0.01 mM EDTA, 0.1M Tris (pH 7.4), and 1% SDS. The supernatant was extracted with phenol-chloroform and ethanol precipitated in the presence of oyster glycogen. Reaction products were electrophoresed on a 5% polyacrylamide sequencing gel containing 8M urea in 1×TBE. Gels were exposed overnight at −70° C. with an intensifying screen.

TRP-185 stimulates gene expression from the HIV LTR

The role of TRP-185 in stimulating in vitro transcription of the HIV LTR was next assayed. In vitro transcription assays were performed with a concentration of magnesium (5 mM) which favored the synthesis of full-length transcripts from the HIV LTR. A wild-type HIV LTR CAT template when restricted with NcoI generates a run-off transcript of 620 bp which is inhibited by 2 μg/ml final concentration of alpha amanitin.

Both wild-type and a TAR mutant containing a deletion of the bulge (+23/+25) were restricted with NcoI. Addition of HeLa cell nuclear extract alone resulted in low level synthesis of the 620 bp RNA species from both the wild-type and (+23/+25) templates (FIG. 8, lanes 1 and 5). There was minimal stimulation of transcription with the addition of the cofactor fraction with the wild-type but not the (+23/+25) template (FIG. 8 lanes 2 and 6). However, the addition of either TRP-185 alone or TRP-185 and cofactor resulted in approximately a four-fold increase in in vitro transcription from the wild-type (FIG. 8, lanes 3 and 4) but not the (+23/+25) construct (FIG. 8, lanes 7 and 8).

Since tat is able to regulate the binding of TRP-185 to TAR RNA, it is critical to determine the function of TRP-185. Addition of TRP-185 to HeLa nuclear extract results in the stimulation of in vitro transcription from the HIV LTR. Though the level of activation is only four-fold, it must be noted that HeLa nuclear extract contains significant amounts of both cofactor and TRP-185. It is likely that a much greater level of transcriptional activation may be obtained with completely reconstituted extracts. In our studies, we were unable to obtain significant additional stimulation by the addition of tat protein to in vitro transcription assays as previously described.[33] The conditions used in our in vitro transcription assays do not address whether TRP-185 is involved primarily in the stimulation of HIV LTR transcriptional initiation and/or elongation.[25] Furthermore, we do not address the role of tat in terms of its role on in vitro transcription of the HIV LTR.

A model consistent with our data and previous studies would suggest that TRP-185 may be a crucial factor for the formation of or efficient processing of the cellular transcription complex assembled on the HIV promoter. In this model, TRP-185 would interact with the loop of the nascent TAR RNA transcribed from the HIV LTR to form a complex which can proceed slowly and as such becomes rate determining. Binding of tat to the bulge region as it arises during the formation of TAR RNA would then cause the release of TRP-185 from the loop region with subsequent catalytic effects on the transcriptional initiation and/or elongation process. The provided in vitro transcription analysis indicates that TRP-185 stimulates gene expression from a wild-type HIV LTR template but not an HIV template containing mutations in TAR. Thus, TRP-185 is a likely candidate for a cellular factor which is regulated by the tat protein and is involved in modulating the level of HIV gene expression.

EXAMPLE 7

Binding of TRP-285 to Cellular Nucleic Acid

The present example is provided to demonstrate the binding affinity which TRP-185 protein may have for cellular nucleic acid species. As TRP-185 is a cellular protein, and in light of the regulatory action the inventors have demonstrated it to have in viral gene expression/binding of viral RNA, it is contemplated by the present inventors that TRP-185 may also be binding a small class of conserved cellular nucleic acid sequences.

Figure 11:
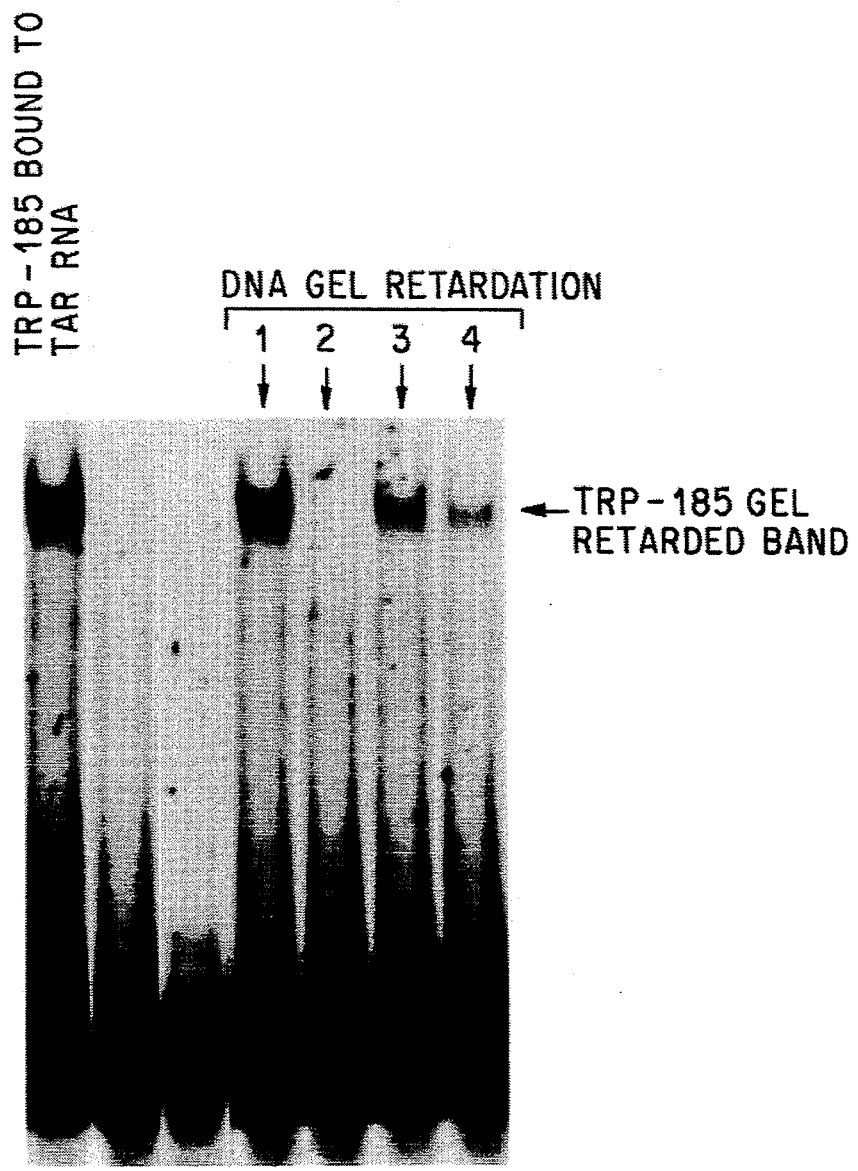

Evidence collected in support of this observation include the molecular "footprinting" of initiation regions of cellular DNA nucleic acid from adenovirus, as well as with HIV DNA, with TRP-185 cellular protein (see FIG. 11).

The inventors demonstrate in this example that highly purified fractions of TRP-185 bind strongly to elements of cellular promoters near the "initiation element". Thus, the TRP-185 cellular protein, already demonstrated to regulate viral promoters, may also regulate cellular promoters. Highly conserved regions of, for example, the adenovirus, located downstream of the promoter region, may also be activated by the binding of a cellular protein, in a manner similar to that of TRP-185, to affect gene expression. TRP-185 does in fact bind downstream of a promoter region to a nucleic acid region which is known to be of a highly conserved sequence. This or a similar mechanism may be acting to bind cellular genes and control cellular gene expression.

PROPHETIC EXAMPLE 8

Proposed Method for Preparing a Therapeutic Agent for the Treatment of Aids

The present prophetic example is provided to outline a method which may be used to treat patients infected with the HIV or HTLV virus. The TRP-185 cellular protein is demonstrated to enhance HIV gene expression by binding a particular TAR region of the HIV RNA LTR. This binding downstream of the promoter region is critical to viral gene expression. Therefore, the use of specific inhibitors of TRP-185 would shut off viral gene expression, thereby serving as a therapeutic agent for persons infected with the virus.

TRP-Inhibitors

ATRP-185 inhibitor as a therapeutic agent for AIDS and related diseases, such as ARC, may be administered as a capsule, as a powder to be reconstituted for subcutaneous or intramuscular administration.

The inhibitor of TRP-185 cellular protein may take the form of an antibody specific for TRP-185 (as described in example 3), a competing protein or peptide which has specific binding affinity for the same TAR RNA binding site, a peptide or protein which dephosphorylates TRP-185 cellular protein, an antisense oligonucleotide specific for the TAR RNA binding site of TRP-185 cellular protein, a DNA or RNA fragment that preferentially binds the TRP-195 protein, or a protein or peptide which acts to modify a TRP-185 protein so as to prevent the binding of the TRP-185 to its specific TAR RAN binding site.

PROPHETIC EXAMPLE 9

Proposed Method for Isolating and Cloning the Gene Encoding TRP-185 Protein

The purification and cloning of TRP-185 and its associated cofactor species will be required to address the potential roles of these proteins in mediating tat activation of the HIV LTR.

Thus, the present prophetic example provides an outline of those procedures which will be employed to accomplish this task.

The methods and procedures outlined in the AMERSHAM®[53] SUPERSCREEN® Immunoscreening protocol may be employed together with the monoclonal antibodies for TRP-185 described herein at example 3. More specifically, the referenced system may be used for screening λ-GT11 libraries with monoclonal antibodies raised to TRP-185 (outlined in Example 3).

Briefly, the human gene encoding the TRP-185 protein of the present invention may be obtained by first obtaining, for example, a human chromosomal cDNA library (Clonetech Laboratories Inc., 4030 Fabian Way, Palo Alto, Calif. 94303). Alternatively, one may prepare their own human chromosomal cDNA library employing those techniques available to those in the art.[54,56] The gene which encodes TRP-185 will be detectable by employing a human chromosomal cDNA library as it is known by the work of the present inventors that TRP-185 is a cellular as opposed to viral protein.

The human chromosomal cDNA library will be screened by allowing the recombinant λ-GT11 phage to grow and to form plaques in top agar in a petri dish using E. coli as the host. The plaques will then be transferred to a, for example, nitrocellulose filter impregnated with IPTG to induce expression, as described in the AMERSHAM® kit.[53] The nitrocellulose filters will then be incubated in the presence of a nonspecific protein. By way of example, such a nonspecific protein would be borne serum albumin (BSA).

The nitrocellulose filters (which include the formed plaques) will then be exposed to the TRP-185 specific antibody prepared as described in Example 3. A second, detectably labeled antibody would also be exposed to the filters. The second antibody would be specific for the TRP-185 specific antibody (the "first" antibody). By way of example, such a second detectably labeled antibody may constitute a horseradish peroxidase labelled second antibody.

Addition of the substrate (for example, the substrate 3.3' diaminobenzidine tetrahydro-chloride (DBA) or hydrogen peroxide where horseradish peroxidase is the detectable label of the second antibody) for the second detectably labeled antibody will provide for the development of a "positive" signal of the TRP-185+plaques. The original plaques formed which correspond to the TRP-185+plagues will then be selected for further purification and rescreening to check and isolate the TRP-185+clones. The DNA sequences from the obtained TRP-185+clones may then be excised and further characterized. Such further characterization may include the preparation of expression vectors containing the DNA from TRP-185+clones. Upon preparation of the expression vectors with the TRP-185 DNA sequence, the protein products expressed may be isolated and tested against a monoclonal antibody specific for the TRP-185 protein (antibody preparation described in Example 3).

According to this method, one skilled in the art of gene cloning and isolation may obtain the human gene encoding the TRP-185 cellular protein which is capable of binding TAR RNA of HIV described in the present invention.

PROPHETIC EXAMPLE 10

Immunodiagnostic Assay for HIV Infection

The present example outlines a method which may be useful for the diagnosis and clinical monitoring of the progression of an HIV infection, such as AIDS, in a human. The method employs the monitoring of the levels of, for example, antibodies specific for the TRP-185 cellular protein. At least two forms of the TRP-185 as antigen will be used in the assay including TRP-185 as antigen without exposure/treatment with a cofactor fraction and with exposure to a cofactor fraction. The presence of antibody specific for each of these TRP-185 forms of antigen in a biological sample, such as blood will then be determined using standard immunoassay techniques.

By determining the presence of antibodies to TRP-185-cofactor exposed antigen and to TRP-185 antigen not exposed to cofactor, the assay may indicate the relative diseased state of the patient during the progression of the disease.

In order to be used as a diagnostic tool for HIV or HTLV infection, a control value for antibody to TRP-185 as antigen in the system of a healthy, non-HIV infected population of samples will be established. TRP-185 is a cellular protein which is present in a normal healthy animal and which also is likely to have a function in the "turning off/turning on" of cellular genes of the animal (see Example 7), apart from its additional action in binding HIV TAR RNA and enhancing viral gene expression.

As an immunodiagnostic assay, an animal sample to be tested would first be obtained and a volume thereof incubated with an amount of TRP-185 cofactor exposed antigen, as well as with an amount of TRP-185 antigen which had not been exposed to antigen.

Preparation of TRP-185 cofactor exposed binding protein as antigen

According to one proposed pretreatment of the TRP-185 as antigen, the preparation of TRP-185 defined in Example 1 may be incubated with cofactor fraction for about 5 minutes at room temperature.

The exposure of TRP-185 binding protein to a cofactor fraction (as defined in Example 2) is expected to chemically change the TRP-185, (perhaps phosphorylate), and therefore potentially change the tertiary structure of the TRP-185 so as to exposed different antigenic sites. Therefore, the exposed/modified TRP-185 could elicit antibodies with specificity that differs from those antibodies elicited by unmodified TRP-185.

Preparation of TRP-185 binding protein as antigen

TRP-185 will be prepared from mammalian cells as described in Example 1.

For this assay, two preparations of monoclonal antibodies would be prepared as described in Example 3, using the cofactor exposed-TRP-185 and cofactor unexposed TRP-185 as antigen. These separate antibody preparations could then be used, along with its corresponding antigen, in establishing the level of either antibody in an animal sample.

A standard curve for each of the TRP-185 antigens which includes an amount of the specific (i.e., antibody against exposed/not exposed) anti-TRP-185 antibody will be prepared.

It is expected that the relative amount of antibody specific for the cofactor exposed TRP-185 antigen will greater than the relative amount of the antibody specific for the TRP-185 antigen (without cofactor exposure) in a biological sample with the increasing progression of an HIV or HTLV infection in the patient. This assay may be used in conjunction with the therapeutic agents of the present invention (Example 8) to monitor the effectiveness of the agent in reducing/eliminating the gene activating form (a phosphorylated form) of the TRP-185 cellular protein.

While those of skill in the art will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

The following references are specifically incorporated herein in pertinent part for the particular purposes indicated.

BIBLIOGRAPHY

1. Rosen, C. A., J. G. Sodroski, and W. A. Haseltine (1985), *Cell*, 41:813-823.
2. Jones, K. A., J. T. Kadonga, P. A. Luciw, and R. Tjian (1986), *Science*, 232:755-759.
3. Garcia, J. A., F. K. Wu, R. Mitsuyasu, and R. B. Gaynor (1987), *EMBO J.*, 6:3761-3770.
4. Nabel, G., and Baltimore (1987), *Nature* (London), 326:711-713.
5. Feng, S., and E. C. Holland (1988), *Nature*, 334:165-167.
6. Jakobovits, A., D. H. Smith, E. B. Jakobovits, and D. J. Capon (1988), *Mol. Cell. Biol.*, 8:2555-2561.
7. Jones, K. A., P. A. Luciw, and N. Duchange (1988), *Genes & Dev.*, 2:1101-1114.
8. Wu, F. K., J. A. Garcia, D. Harrich, and R. B. Gaynor (1988), *EMBO J.*, 7:2117-2130.
9. Berkhout, B., and K. T. Jeang (1989), *J. Virol.*, 63:5501-5504.
10. Garcia, J. A., D. Harrich, E. Soultanakis, F. Wu, R. Mitsuyasu, and R. B. Gaynor (1989), *EMBO J.*, 8:765-778.
11. Harrich, D., J. Garcia, F. Wu, R. Mitsuyasu, and R. B. Gaynor (1989), *J. Virol.*, 63:2585-2591.
12. Hauber, J., and B. R. Cullen (1988), *J. Virol.*, 62:673-679.
13. Selby, M. J., E. S. Bain, P. A. Luciw, and B. M. Peterlin (1989), *Genes & Dev.*, 3:547-558.
14. Ratnasabapathy, R., M. Sheldon, L. Johal, and N. Hernandez (1990), *Genes & Dev.*, 4:2061-2074.
15. Roy, S., N. T. Parkin, C. Rosen, J. Itovitch, and N. Sonenberg (1990a), *J. Virol.*, 64:1402-1406.
16. Roy, S., U. Delling, C. H. Chen, C. A. Rosen, and N. Sonenberg (1990b), *Genes & Dev.*, 4:1365-1373.

17. Siekevitz, M., S. F. Josephs, M. Dukovich, N. Peffer, F. Wong-Staal, and W. Greene (1987), *Science*, 238:1575-1578.
18. Crabtree, G. R. (1989), *Science*, 243:355-361.
19. Tong-Starksen, S. E., P. A. Luciw, and B. M. Peterlin (1987), *Proc. Natl. Acad. Sci. U.S.A.*, 84:6845-6851.
20. Braddock, M., A. Chambers, W. Wislon, M. P. Esnouf, S. E. Adams, A. J. Kingsman and S. M. Kingsman (1989), *Cell*, 58:269-279.
21. Harrich, D., J. Garcia, R. Mitsuyasu, and R. B. Gaynor (1990), *EMBO J.*, 9:4417-4424.
22. Haseltine (1986), *Cell*, 44:941-947.
23. Fisher, A. G., M. B. Feinberg, S. F. Josephs, M. E. Harper, L. M. Marselle, G. Reyes, M. A. Gonda, A. Aldovini, C. Debouk, R. C. Gallo, and F. Wong-Staal (1986), *Nature*, 320:367-371.
24. Rice, A. P., and M. B. Mathews (1988), *Nature* (London), 332:551-553.
25. Laspia, M. F., A. P. Rice, and M. B. Mathews (1989), *Cell*, 59:283-292.
26. Marciniak, R. A., M. A. Garcia-Blanco. and P. A. Sharp (1990), *Proc. Natl. Acad. Sci.*, 87:3624-3628.
27. Berkhout, B., R. H. Silverman, and K. T. Jeang (1989), *Cell*, 59:273-282.
28. Dingwall, C., I. Ernberg, M. J. Gait, S. M. Green, S. Heaphy, J. Karn, A. D. Lowe, M. Singh, M. A. Skinner (1990), *EMBO J.*, 9:4145-4153.
29. Dingwall, C., I. Ernberg, M. J. Gait, S. M. Green, S. Heaphy, J. Karn, A. D. Lowe, M. Singh, M. A. Skinner, and R. Vallerio (1989), *Proc. Natl. Acad. Sci.*, 86:6925-6929.
30. Weeks, K. M., C. Ampe, S. C. Schultz, T. A. Steitz, and D. M. Crothers (1990), *Science*, 249:1281-1285.
31. Gatignol, A., A. Kumar, A. Rabson, and K. T. Jeang (1989), *Proc. Natl. Acad. Sci.*, 86: 7828-7832.
32. Gaynor, R., E. Soultanakis, M. Kuwabara, J. Garcia, and D. S. Sigman. (1989), *Proc. Natl. Acad. Sci.*, 86:4858-4862.
33. Marciniak, R. A., B. J. Calnan, A. D. Frankel, and P. A. Sharp (1990), *Cell*, 63: 791-802.
34. Goodman and Gilmans, *The Pharmacological Basis of Therapeutics*, 8th Ed. (1990), Gilman, Rall, Niesand, Taylor, editors: pp 1182-1201.
35. Dignam, J. D., R. M. Lebovitz, and R. G. Roeder (1983), *Nucl. Acids. Res.*, 11:1475-1489.
36. Jakobovits, A., A. Rosenthal, and D. J. Capon (1990), *EMBO J.*, 9:1165-1170.
37. Southgate, C., M. L. Zapp, and M. R. Green (1990), *Nature*, 345:640-642.
38. Bhattacharyya, A., A. I. H. Murchie, and D. M. J. Lilley (1990), *Nature*, 343:484-487.
39. Takagaki, Y., J. L. Manley, C. C. MacDonald, J. Wilusz, and T. Shenk (1990), *Genes & Dev.*, 4:2112-2120.
40. Wilusz, J., T. Shenk, Y. Takagaki, and J. L. Manley (1990), *Mol. Cell. Biol.*, 10:1244-1248.
41. Baker, R. E., O. Gabrielsen, and B. D. Hall (1986), *J. Biol. Chem*, 261:5275-5282.
42. Lazinski, D., E. Grzadzielska, and A. Das (1989), *Cell*, 59:207-218.
43. Gorman, C. M., L. F. Moffat, and B. H. Howard, (1982) *Mol Cell. Biol.*, 2:1044-1051.
44. Selby, M. J., and B. M. Peterlin (1990), *Cell*, 62:769-776.
45. Modesti, N., J. A. Garcia, C. Debouck, B. M. Peterlin, and R. Gaynor (1991), *New Biologist*, 3:759-768.
46. Cullen, B. R. (1986), *Cell*, 46:423-426.
47. Field et al. (1988), *Molecular and Cellular Biology*, 8(5): 2159-2165.
48. Smith and Johnson (1988), *Gene*, 67: 31-40.
49. Calnan, B. J., S. Biancalana, D. Hudson, and A. D. Frankel (1991), *Genes and Development* 5:201-210.
50. Gaynor, R. (1991), *Advances in Mol. Biol. and Targeted Treatment for AIDS*, A. Kumar, Ed. Plenum Press, New York. pp 79-90.
51. Harlow, E. and D. Lane. (1988) *Antibodies, a Laboratory Manual.* Cold Spring Harbor Laboratory
52. Fields et al., editors (1985), *Fundamental Virology*; Raven Press, pp. 681-707.
53. AMERSHAM® Catelog, SUPERSCREEN Immunoscreening System (1991)
54. Kimmel, A. R. and Berger, S. L. (1987) *Meth. Enzymol.*, 152:307.
55. Okayama, H. and Berg. P. (1982) *Mol. Cell. Biol.*, 2:161.
56. Gubler, U. and Hoffman, B. J. (1983), *Gene*, 25:283.
57. Smale, S. T. and Baltimore (1989), *Cell*, 57:103-115.

What is claimed is:

1. A nucleic acid binding element obtained from mammalian cells susceptible to infection with HIV comprising a TRP-185 cellular protein that binds with high affinity to a TAR bulge and loop region of an HIV RNA in the presence of a cofactor fraction having a molecular weight of about 85-100 kD by sucrose gradient analysis, said TRP-185 cellular protein having a molecular weight of about 175-190 kD by sucrose gradient analysis.

2. The nucleic acid binding element of claim 1 wherein said cellular protein is designated TRP-185.

3. The nucleic acid binding element of claim 2 wherein said cellular protein binds to a TAR region of an HIV mRNA with an affinity of about $3 \times 10^{-10}$M.

4. The nucleic acid binding element of claim 3 wherein said cellular protein increases transcription of wild type HIV LTR about 4-fold.

5. The nucleic acid binding element of claim 1 wherein the TAR region is a transactivating region.

6. The nucleic acid binding element of claim 1 wherein the TAR region is at least a 12 base pair segment of the TAR mRNA.

7. The nucleic acid binding element of claim 6 wherein the cellular protein binds a base pair segment between bases 23-34 of the TAR mRNA.

8. The nucleic acid binding element of claim 1 further defined having a molecular weight of about 185 kD.

9. The nucleic acid binding element of claim 1 prepared by a process comprising the steps of:
   obtaining a volume of mammalian cells susceptible to infection by HIV;
   preparing a nuclear extract from the mammalian cells;
   fractionating the nuclear extract and selecting fractions having HIV TAR binding activity; and
   isolating an element having a molecular weight of between 175-190 kD from the selected fractions to provide a nucleic acid binding element.

10. The nucleic acid binding element of claim 9 wherein preparing a nuclear extract of mammalian cells comprises:

slicing a cell pellet of mammalian cells susceptible to infection with HIV with a cell homogenizer;
isolating cell nuclei;
lysing the nuclei to obtain a lysate;
separating a supernatant from the lysate; and
isolating a nuclear extract from the supernatant, said nuclear extract having a binding activity for a TAR region of a nucleic acid.

11. The nucleic acid binding element of claim 9 wherein the steps for fractionating the nuclear extract includes:

chromatographing the nuclear extract on heparin agarose;
eluting the chromatographed nuclear extract with potassium chloride to obtain fractions having TAR binding activity;
preparing a dialyzate of the fractions having TAR binding activity;
chromatographing the dialyzate on an anionic separation gel;
precipitating TAR active binding fractions from the anionic separation gel with ammonium sulfate;
applying the TAR active binding fractions to a molecular weight separation column;
collecting TAR active binding fractions and applying a dialyzate thereof to a molecular weight separation column;
collecting TAR active binding fractions and applying a dialyzate thereof to a anionic separation column;
collecting TAR active binding fractions and applying a dialyzate thereof to a anionic separation column;
collecting TAR active binding fractions and applying a dialyzate of selected washed fractions to a continuous sucrose gradient; and
isolating a nucleic acid binding element having a molecular weight of between 175 kD–190 kD as determined by a continuous sucrose gradient and having TAR region binding activity.

12. The nucleic acid binding element of claims 1, 9 or 10 wherein the cellular protein is obtained from a HeLa cell nuclear extract.

13. The nucleic acid binding element of claim 11 wherein the cellular protein is designated TRP-185 and is obtained in a preparation from HeLa cells at an about 3,000-fold purification.

14. A TRP-185 nucleic acid binding protein having a molecular weight of between about 175 kD–190 kD as determined by continuous sucrose gradient and having high binding affinity to a bulge and loop TAR region of HIV mRNA in the presence of a cofactor fraction, said cofactor fraction having a molecular weight of about 100 kD as determined by continuous sucrose gradient.

15. The TRP-185 nucleic acid binding protein of claim 14 wherein the co-factor fraction enhances the binding of the TRP-185 to the TAR region of HIV mRNA.

16. A nucleic acid binding protein TRP-185 prepared by a process comprising the steps of:

obtaining a volume of HeLa cells;
preparing a nuclear extract;
fractionating the nuclear extract; and
isolating the nucleic acid binding protein comprising the TRP-185 protein from the nuclear extract fractions, said TRP-185 protein having a molecular weight of between about 175 kD–190 kD and also having binding affinity to a TAR bulge and loop region of HIV mRNA.

* * * * *